(12) United States Patent  
Mandal et al.

(10) Patent No.: US 8,198,322 B2  
(45) Date of Patent: Jun. 12, 2012

(54) APOPTOTIC AND ANTI-TUMOR ACTIVITIES OF METALLO-SALENS

(75) Inventors: Subhrangsu S. Mandal, Arlington, TX (US); Khairul I. Ansari, Arlington, TX (US); James D. Grant, III, Austin, TX (US)

(73) Assignee: Board of Regents, The University of Texas System, Austin, TX (US)

( * ) Notice: Subject to any disclaimer, the term of this patent is extended or adjusted under 35 U.S.C. 154(b) by 217 days.

(21) Appl. No.: 12/491,103

(22) Filed: Jun. 24, 2009

(65) Prior Publication Data

US 2009/0326061 A1 Dec. 31, 2009

Related U.S. Application Data

(60) Provisional application No. 61/163,575, filed on Mar. 26, 2009, provisional application No. 61/075,378, filed on Jun. 25, 2008.

(51) Int. Cl.
*A61K 31/28* (2006.01)
*C07F 19/00* (2006.01)

(52) U.S. Cl. ............... 514/492; 556/32; 514/502

(58) Field of Classification Search .......... 556/32; 514/492, 502
See application file for complete search history.

(56) References Cited

U.S. PATENT DOCUMENTS

| | | | |
|---|---|---|---|
| 5,618,957 A * | 4/1997 | Hubner et al. | 556/32 |
| 5,834,509 A * | 11/1998 | Malfroy-Camine et al. | 514/492 |
| 6,300,521 B1 * | 10/2001 | Klatt et al. | 568/312 |
| 7,122,537 B2 | 10/2006 | Malfroy-Camine et al. | |
| 2007/0142462 A1 | 6/2007 | Kennedy | |
| 2007/0275944 A1 | 11/2007 | Sharpe | |

OTHER PUBLICATIONS

Basu, A.; Miura, A. Int J Mol Med 2002, 10, 541-5.
Barnes, K. R.; Lippard, S. J. Met Ions Biol Syst 2004, 42, 143-77.
Zhang, C. X.; Lippard, S. J. Current Opinion in Chemical Biology 2003, 7, 481-89.
Brambilla, C.; Ferrari, L.; Passoni, P.; Bonadonna, G. Cancer Treat Rev 1993, 19 Suppl C, 3-9.
Robson, H.; Meyer, S.; Shalet, S. M.; Anderson, E.; Roberts, S.; Eden, O. B. Med Pediatr Oncol 2002, 39, 573-80.
Zhang, L.; Zhang, Y.; Huang, P. Y.; Xu, F.; Peng, P. J.; Guan, Z. Z. Cancer Chemother Pharmacol 2008, 61, 33-8.
Boerner, L. J. K.; Zaleski, J. M. Current Opinion in Chemical Biology 2005, 9, 135-44.
Ansari, K. I.; Mishra, B. P.; Mandal, S. S. Biochim Biophys Acta 2008, 1779, 66-73.
Baruah, H.; Barry, C. G.; Bierbach, U. Current Topics in Medicinal Chemistry 2004, 4, 1537-49.
Chow, C. S.; Barton, J. K. Methods in Enzymology 1992, 212, 219-42.
Denison, C.; Kodadek, T. Chem Biol 1998, 5, R129-45.
Dickinson, L. A.; Burnett, R.; Melander, C.; Edelson, B. S.; Arora, P. S.; Dervan, P. B.; Gottesfeld, J. M. Chem Biol 2004, 11, 1583-94.
Fechter, E. J.; Olenyuk, B.; Dervan, P. B. Angew Chem Int Ed Engl 2004, 43, 3591-4.
Guo, Z.; Zhou, D.; Schultz, P. G. Science 2000, 288, 2042-5.
Hartinger, C. G.; Schluga, P.; Galanski, M.; Baumgartner, C.; Timerbaev, A. R.; Keppler, B. K. Electrophoresis 2003, 24, 2038-44.
Kwon, Y.; Arndt, H. D.; Mao, Q.; Choi, Y.; Kawazoe, Y.; Dervan, P. B.; Uesugi, M. J Am Chem Soc 2004, 126, 15940-1.
Majmudar, C. Y.; Mapp, A. K. Curr Opin Chem Biol 2005, 9, 467-74.
Mapp, A. K.; Ansari, A. Z.; Ptashne, M.; Dervan, P. B. Proc Natl Acad Sci USA 2000, 97, 3930-5.
Murphy, C. J.; Barton, J. K. Methods Enzymol 1993, 226, 576-94.
Ott, I.; Gust, R. Arch Pharm (Weinheim) 2007, 340, 117-26.
Perrin, D. M.; Mazumder, A.; Sigman, D. S. Progress in Nucleic Acid Research and Molecular Biology, vol. 52 1996, 52, 123-51.
Zheng, P.; Tang, N.; Burrows, C. J.; Rokita, S. E. Faseb Journal 1994, 8, A1265-a1265.
Zorbas, H.; Keppler, B. K. Chembiochem 2005, 6, 1157-66.
Jacobsen, E. N.; Zhang, W.; Guler, M. L. Journal of the American Chemical Society 1991, 113, 6703-04.
Bhattacharya, S.; Mandal, S. S. Chemical Communications 1996, 1515-16.
Burrows, C. J.; Hickerson, R. P.; Muller, J. G.; Felden, B.; Rokita, S. E. Biophysical Journal 1999, 76, A5-a5.
Czlapinski, J. L.; Sheppard, T. L. Journal of the American Chemical Society 2001, 123, 8618-19.
Muller, J. G.; Paikoff, S. J.; Rokita, S. E.; Burrows, C. J. J Inorg Biochem 1994, 54, 199-206.
Routier, S.; Bernier, J. L.; Waring, M. J.; Colson, P.; Houssier, C.; Bailly, C. Journal of Organic Chemistry 1996, 61, 2326-31.
Doctrow, S. R.; Huffman, K.; Marcus, C. B.; Tocco, G.; Malfroy, E.; Adinolfi, C. A.; Kruk, H.; Baker, K.; Lazarowych, N.; Mascarenhas, J.; Malfroy, B. J Med Chem 2002, 45, 4549-58.
Gravert, D. J.; Griffin, J. H. Journal of Organic Chemistry 1993, 58, 820-22.
Shrivastava, H. Y.; Devaraj, S. N.; Nair, B. U. Journal of Inorganic Biochemistry 2004, 98, 387-92.
Rokita, S. E.; Burrows, C. J. 2003, 1, 126-45.
Routier, S.; Vezin, H.; Lamour, E.; Bernier, J. L.; Catteau, J. P.; Bailly, C. Nucleic Acids Research 1999, 27, 4160-66.
Rong, Y.; Doctrow, S. R.; Tocco, G.; Baudry, M. Proc Natl Aced Sci USA 1999, 96, 9897-902.
Woldemariam, G. A.; Mandal, S. S. J Inorg Biochem 2008, 102, 740-7.
Gerloch, M., Lewis, J., Mabbs F. E., Richards, A. Journal of the Chemical Society [section] A: Inorganic, Physical and Theoretical 1968, 1, 112-16.

(Continued)

*Primary Examiner* — Porfirio Nazario Gonzalez
(74) *Attorney, Agent, or Firm* — Winstead PC

(57) ABSTRACT

The present invention describes the synthesis and biochemical activities of metallo-salen compounds and their derivatives. The Mn(III)-salen and Fe(III)-salen derivatives of the present invention are potential anti-tumor agents, that affect cell viability, induce strong apoptotic activity, cause nuclear condensation, fragmentation, and ultimately death in breast cancer cells MCF-7.

8 Claims, 16 Drawing Sheets

OTHER PUBLICATIONS

Gravert, D. J.; Griffin, J. H. Metal Ions in Biological Systems, vol. 33 1996, 33, 515-36.

Pavri, R.; Zhu, B.; Li, G.; Trojer, P.; Mandal, S.; Shilatifard, A.; Reinberg, D. Cell 2006, 125, 703-17.

Zhu, B.; Mandal, S. S.; Pham, A. D.; Zheng, Y.; Erdjument-Bromage, H.; Batra, S. K.; Tempst, P.; Reinberg, D. Genes Dev 2005, 19, 1668-73.

Mandal, G. W. a. S. S. J. Inorg. Biochem 2007, In Press.

Awasthi, S.; Singhal, S. S.; He, N.; Chaubey, M.; Zimniak, P.; Srivastava, S. K.; Singh, S. V.; Awasthi, Y. C. Int J Cancer 1996, 68, 333-9.

Nguyen S. M., L., C J., and Levin, L A. Journal of Neuroscience 2007, 161, 281-84.

Park, M. S.; De Leon, M.; Devarajan, P. Journal of the American Society of Nephrology 2002, 13, 858-65.

Ansari, A. Z.; Mapp, A. K. Current Opinion in Chemical Biology 2002, 6, 765-72.

Balamurugan, K.; Rajaram, R.; Ramasami, T.; Narayanan, S. Free Radical Biology and Medicine 2002, 33, 1622-40.

Barton, J. K. Science 1986, 233, 727-34.

Borchardt, A.; Liberles, S. D.; Biggar, S. R.; Crabtree, G. R.; Schreiber, S. L. Chem Biol 1997, 4, 961-8.

Copeland, K. D.; Lueras, A. M.; Stemp, E. D.; Barton, J. K. Biochemistry 2002, 41, 12785-97.

Danford, A. J.; Wang, D.; Wang, Q.; Tullius, T. D.; Lippard, S. J. Proc Natl Acad Sci USA 2005, 102, 12311-6.

Dias, N.; Jacquemard, U.; Baldeyrou, B.; Tardy, C.; Lansiaux, A.; Colson, P.; Tanious, F.; Wilson, W. D.; Routier, S.; Merour, J. Y.; Bailly, C. Biochemistry 2004, 43, 15169-78.

Gottesfeld, J. M.; Neely, L.; Trauger, J. W.; Baird, E. E.; Dervan, P. B. Nature 1997, 387, 202-5.

Liu, B.; Alluri, P. G.; Yu, P.; Kodadek, T. J Am Chem Soc 2005, 127, 8254-5.

Mapp, A. K. Org Biomol Chem 2003, 1, 2217-20.

Minter, A. R.; Brennan, B. B.; Mapp, A. K. J Am Chem Soc 2004, 126, 10504-5.

Mote, J., Jr.; Ghanouni, P.; Reines, D. J Mol Biol 1994, 236, 725-37.

Pyle, A. M.; Barton, J. K. Progress in Inorganic Chemistry 1990, 38, 413-475.

Schreiber, S. Curr Biol 2004, 14, R292-3.

Meares, C. F.; Datwyler, S. A.; Schmidt, B. D.; Owens, J.; Ishihama, A. Methods Enzymol 2003, 371, 82-106.

Ozoline, O. N.; Fujita, N.; Ishihama, A. J Biol Chem 2000, 275, 1119-27.

Kurahashi, T.; Kobayashi, Y.; Nagatomo, S.; Tosha, T.; Kitagawa, T.; Fujii, H. Inorg Chem 2005, 44, 8156-66.

\* cited by examiner

R7-10 = = OH, OCH3, OCH2CH3, OCH2CH2CH3, O-isopropyl, X=O-Butyl
  = Cl, Br, F
  = NO2
  = CH3, -CH2CH3, -CH2CH2CH3, -isopropyl, -Butul
  = -Phenyl
  = SH
  = COOH, COOH3, COOCH2CH3

X = OH, OCH3, OCH2CH3, OCH2CH2CH3, O-isopropyl, X= O-Butyl
 = Cl, Br, F
 = NO2
 = CH3, -CH2CH3, -CH2CH2CH3, -isopropyl, -Butul
 = -Phenyl
 = SH
 = COOH, COOH3, COOCH2CH3

APOPTOTIC AND ANTI-TUMOR ACTIVITIES OF METALLO-SALENS

CROSS-REFERENCE TO RELATED APPLICATIONS

This application claims benefit of U.S. Provisional Applications No. 61/075,378 and 61/163,575 filed on Jun. 25, 2008, and Mar. 26, 2009, respectively which are incorporated herein by reference in their entirety.

TECHNICAL FIELD OF THE INVENTION

The present invention relates in general to the field of metallo-salens and metallo-salen derivatives, and more particularly to the synthesis of Mn(III)- and Fe(III)-salen derivatives and their effects on human cancer and non-cancer cells.

STATEMENT OF FEDERALLY FUNDED RESEARCH

None.

INCORPORATION-BY-REFERENCE OF MATERIALS FILED ON COMPACT DISC

None.

BACKGROUND OF THE INVENTION

Without limiting the scope of the invention, its background is described in connection with the use of metallo-salens and metallo-salen derivatives as potential therapeutic agents.

U.S. Pat. No. 7,122,537 issued to Malfroy-camine and Doctrow (2006) describes antioxidant cyclic salen-metal compounds. The '537 patent describes compositions of such antioxidant cyclic salen-metal compounds having superoxide activity, catalase activity and/or peroxidase activity and methods of using such antioxidant cyclic salen-metal compositions to treat or prevent a disease associated with cell or tissue damage produced by free radicals, such as superoxide.

United States Patent Application No. 20070142462 (Kennedy, 2007) discloses methods for treating cancer including administering a patient needing treatment a therapeutically effective amount of one or more antioxidants selected from the group of catalase, N-acetylcysteine, glutathione peroxidase, salen-transition metal complexes, dicumarol, and derivatives thereof.

United States Patent Application No. 20070275944 (Sharpe, 2007) relates to compounds and compositions to treat some neurodegenerative diseases. In some embodiments, the invention relates to an antioxidant comprising a selenium atom and nitroxide group. In further embodiments, the antioxidant comprises peroxidase and superoxide dismutase activity. In some embodiments, the antioxidants are effective in treating neurodegenerative diseases including, but not limited to, Alzheimer's disease, Parkinson's disease, or multiple sclerosis. In additional embodiments, the invention relates to using compounds disclosed herein as free radical electromagnetic imaging agents.

SUMMARY OF THE INVENTION

The present invention describes the synthesis, the biochemical activities, and the uses of metallo-salens and their derivatives as anti-tumor agents. The Mn(III)-salen and Fe(III)-salen derivatives of the present invention affect cell viability, induce strong apoptotic activity, cause nuclear condensation, fragmentation, and ultimately death in breast cancer cells MCF-7.

In one embodiment the present invention describes a compound (I) having formula,

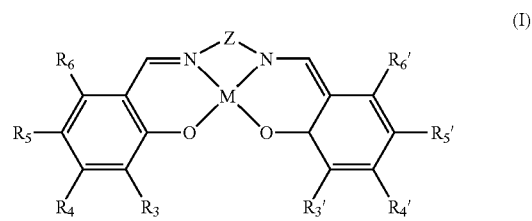

(I)

wherein the Z is selected from a group comprising $-(CH_2)_2$, phenyl, naphthyl, $-(CH_2)_3$, $-C(CH_2)_4$, and benzoic acid, M is a metal selected from a group comprising Fe, Mn, Cu, Ni, Hg, Pt, Sc, Ti, V, Cr, Co, Zn, Y, Zr, Nb, Mo, Tc, Ru, Rh, Pd, Ag, Cd, Lu, Hf, Ta, W, Re, Os, Ir, Pt, and Au, $R_3$ and $R_3'$ are independently selected from a hydrogen, a hydroxyl group and a methoxy group, $R_4$ and $R_4'$ are independently selected from a hydrogen, a hydroxyl group and a methoxy group, $R_5$ and $R_5'$ are independently selected from a hydrogen, a hydroxyl group and a methoxy group, and $R_6$ and $R_6'$ are hydrogens.

In one aspect the Z is selected from a group comprising $-(CH_2)_2$, $-(CH_2)_3$, and $-(CH_2)_4$, M is Mn, Mn(II), Mn(III), Fe, Fe(II) or Fe(II), $R_3$ and $R_3'$ are hydroxyl groups, and $R_4$, $R_4'$, $R_5$, and $R_5'$ are hydrogens. In another aspect the Z is selected from a group comprising $-(CH_2)_2$, $-(CH_2)_3$, and $-(CH_2)_4$, M is Mn, Mn(II), Mn(III), Fe, Fe(II) or Fe(III), $R_4$ and $R_4'$ are hydroxyl groups, and $R_3$, $R_3'$, $R_5$ and $R_5'$ are hydrogens. In yet another aspect the Z is selected from a group comprising $-(CH_2)_2$, $-(CH_2)_3$, and $-(CH_2)_4$, M is Mn, Mn(II), Mn(III), Fe, Fe(II) or Fe(III), $R_5$ and $R_5'$ are hydroxyl groups, and $R_3$, $R_3'$, $R_4$, and $R_4'$ are hydrogens.

In one aspect the Z is selected from a group comprising $-(CH_2)_2$, $-(CH_2)_3$, and $-(CH_2)_4$, M is Mn, Mn(II), Mn(III), Fe, Fe(II) or Fe(III), $R_3$ and $R_3'$ are methoxy groups, and $R_4$, $R_4'$, $R_5$, and $R_5'$ are hydrogens. In another aspect the Z is selected from a group comprising $-(CH_2)_2$, $-(CH_2)_3$, and $-(CH_2)_4$, M is Mn, Mn(II), Mn(III), Fe, Fe(II) or Fe(III), $R_4$ and $R_4'$ are methoxy groups, and $R_3$, $R_3'$, $R_5$, and $R_5'$ are hydrogens. In yet another aspect Z is selected from a group comprising $-(CH_2)_2$, $-(CH_2)_3$, and $-(CH_2)_4$, M is Mn, Mn(II), Mn(III), Fe, Fe(II) or Fe(III), $R_5$ and $R_5'$ are methoxy groups, and $R_3$, $R_3'$, $R_4$, and $R_4'$ are hydrogens.

In one aspect the Z is selected from a group comprising phenyl, naphthyl, and benzoic acid, M is Mn, Mn(II), Mn(III), Fe, Fe(II) or Fe(III), $R_3$ and $R_3'$ are hydroxyl groups, and $R_4$, $R_4'$, $R_5$, and $R_5'$ are hydrogens. In another aspect the Z is selected from a group comprising phenyl, naphthyl, and benzoic acid, M is Mn, Mn(II), Mn(III), Fe, Fe(II) or Fe(III), $R_4$ and $R_4'$ are hydroxyl groups, and $R_3$, $R_3'$, $R_5$, and $R_5'$ are hydrogens. In yet another aspect the Z is selected from a group comprising phenyl, naphthyl, and benzoic acid, M is Mn, Mn(II), Mn(III), Fe, Fe(II) or Fe(III), $R_5$ and $R_5'$ are hydroxyl groups, and $R_3$, $R_3'$, $R_4$, and $R_4'$ are hydrogens.

In one aspect the Z is selected from a group comprising phenyl, naphthyl, and benzoic acid, M is Mn, Mn(II), Mn(III), Fe, Fe(II) or Fe(III), $R_3$ and $R_3'$ are methoxy groups, and $R_4$, $R_4'$, $R_5$, and $R_5'$ are hydrogens. In another aspect the Z is selected from a group comprising phenyl, naphthyl, and benzoic acid, M is Mn, Mn(II), Mn(III), Fe, Fe(II) or Fe(III), $R_4$ and $R_4'$ are methoxy groups, and $R_3$, $R_3'$, $R_5$, and $R_5'$ are hydrogens. In yet another aspect Z is selected from a group comprising phenyl, naphthyl, and benzoic acid, M is Mn, Mn(II), Mn(III), Fe, Fe(II) or Fe(III), $R_5$ and $R_5'$ are methoxy groups, and $R_3$, $R_3'$, $R_4$, and $R_4'$ are hydrogens.

In another embodiment the present invention describes a method of synthesizing a metallo-salen compound and its derivatives by mixing an aldehyde selected from a group comprising salicylaldehyde, 2,3-dihydroxybenzaldehyde, 2,4-dihydroxybenzaldehyde, 2,5-dihydroxybenzaldehyde, 2-hydroxy-3-methoxybenzaldehyde, 2-hydroxy-4-methoxybenzaldehyde, and 2-hydroxy-5-methoxybenzaldehyde and a diamine or a diamino derivative selected from a group comprising ethylenediamine, o-phenylenediamine, phenylenediamine, 2,3-diaminonaphthalene, 1,3-diaminobutane, 1,4-diaminobutane, and 3,4-diaminobenzoic acid dissolved in an organic solvent to form a precipitate. The precipitate formed is filtered and washed with the organic solvent. The precipitate is dissolved in the organic solvent and mixed with an anhydrous metal dissolved in the organic solvent to form a liquid reaction mixture which is heated with stirring to form the metallo-salen compound (I)

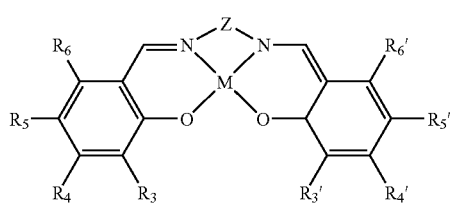

(I)

wherein, Z is selected from a group comprising —$(CH_2)_2$, phenyl, naphthyl, —$(CH_2)_3$, —$(CH_2)_4$, and benzoic acid; M is a metal selected from a group comprising Fe, Mn, Cu, Ni, Hg, Pt, Sc, Ti, V, Cr, Co, Zn, Y, Zr, Nb, Mo, Tc, Ru, Rh, Pd, Ag, Cd, Lu, Hf, Ta, W, Re, Os, Ir, Pt, and Au; $R_3$ and $R_3'$ are independently selected from a hydrogen, a hydroxyl group and a methoxy group; $R_4$ and $R_4'$ are independently selected from a hydrogen, a hydroxyl group and a methoxy group; $R_5$ and $R_5'$ are independently selected from a hydrogen, a hydroxyl group and a methoxy group; and $R_6$ and $R_6'$ are hydrogens. The synthesized metallo-salen compound (I) is precipitated by cooling the liquid reaction mixture or by adding diethyl ether and isolated by filtration or other physical separation method. Finally the isolated metallo-salen compound (I) is recrystallized by dissolving in the organic solvent.

In one aspect of the method of the present invention the organic solvent comprises methanol, ethanol, acetone, isopropyl alcohol, acetonitrile, benzene, ethyl acetate or any combinations thereof. In another aspect the anhydrous metal is in the form of a salt, wherein the salt comprises an anion selected from a group comprising a chloride, an acetate, a halide, a carbonate, a nitrite, a nitrate, a perchlorate, a sulfate, a sulfide, and a hydroxide.

In yet another embodiment the present invention is a pharmaceutical composition comprising

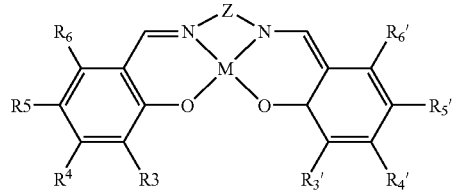

(I)

wherein, Z is selected from a group comprising —$(CH_2)_2$, phenyl, naphthyl, —$(CH_2)_3$, —$(CH_2)_4$, and benzoic acid; M is a metal selected from a group comprising Fe, Mn, Cu, Ni, Hg, Pt, Sc, Ti, V, Cr, Co, Zn, Y, Zr, Nb, Mo, Tc, Ru, Rh, Pd, Ag, Cd, Lu, Hf, Ta, W, Re, Os, Ir, Pt, and Au; $R_3$ and $R_3'$ are independently selected from a hydrogen, a hydroxyl group and a methoxy group; $R_4$ and $R_4'$ are independently selected from a hydrogen, a hydroxyl group and a methoxy group; $R_5$ and $R_5'$ are independently selected from a hydrogen, a hydroxyl group and a methoxy group; and $R_6$ and $R_6'$ are hydrogens.

In one aspect the composition is effective to treat a cancer, selected from a lymphoma, a blastoma, a tumor, a melanoma, ovarian cancer, breast cancer, non-small cell lung cancer, small cell lung cancer, renal cancer, colorectal cancer, pancreatic cancer, gastric cancer, bladder cancer, uterine cancer, lymphoma, and prostrate cancer.

In one embodiment the present invention discloses a method for treating a cancer in an subject comprising the steps of: (i) identifying a subject in need for treatment against the cancer and (ii) providing a therapeutically effective amount of a composition sufficient to treat the cancer comprising:

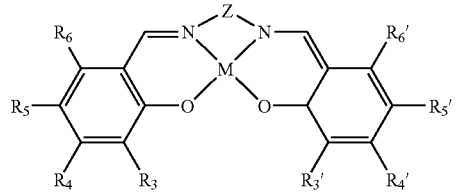

(I)

wherein, Z is selected from a group comprising —$(CH_2)_2$, phenyl, naphthyl, —$(CH_2)_3$, —$(CH_2)_4$, and benzoic acid; M is a metal selected from a group comprising Fe, Mn, Cu, Ni, Hg, Pt, Sc, Ti, V, Cr, Co, Zn, Y, Zr, Nb, Mo, Tc, Ru, Rh, Pd, Ag, Cd, Lu, Hf, Ta, W, Re, Os, Ir, Pt, and Au; $R_3$ and $R_3'$ are independently selected from a hydrogen, a hydroxyl group and a methoxy group; $R_4$ and $R_4'$ are independently selected from a hydrogen, a hydroxyl group and a methoxy group; $R_5$ and $R_5'$ are independently selected from a hydrogen, a hydroxyl group and a methoxy group; and $R_6$ and $R_6'$ are hydrogens.

In one aspect of the method of treatment of the present invention the cancer comprises a melanoma, ovarian cancer, breast cancer, non-small cell lung cancer, small cell lung cancer, renal cancer, colorectal cancer, pancreatic cancer, gastric cancer, bladder cancer, uterine cancer, lymphoma, and prostrate cancer.

BRIEF DESCRIPTION OF THE DRAWINGS

For a more complete understanding of the features and advantages of the present invention, reference is now made to the detailed description of the invention along with the accompanying figures and in which.

DETAILED DESCRIPTION OF THE INVENTION

Figure 1:
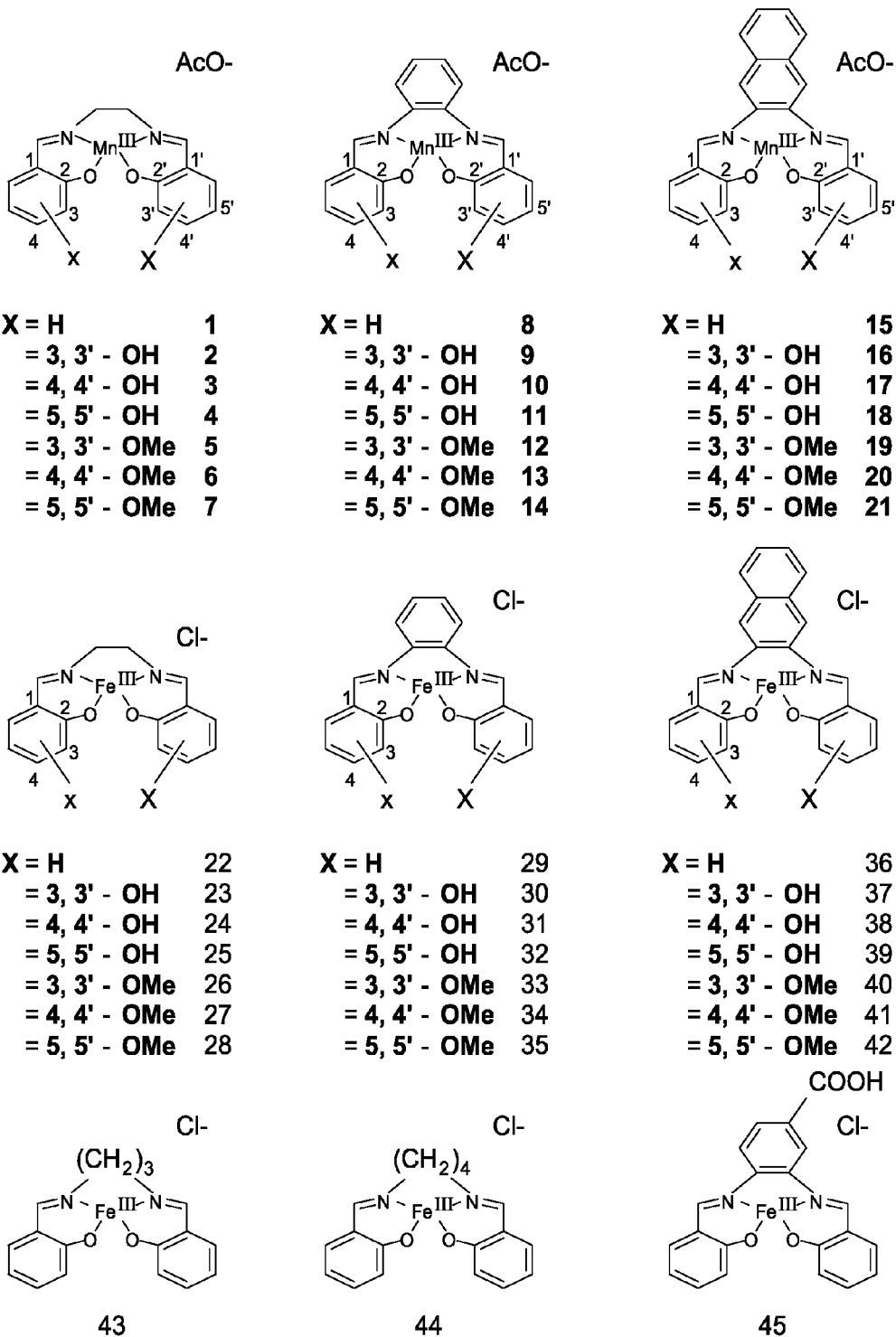
FIG. 1 shows the structures of Mn(III)-salen, Fe(III)-salen and their derivatives (compounds 1-45) of the present invention.

While the making and using of various embodiments of the present invention are discussed in detail below, it should be appreciated that the present invention provides many applicable inventive concepts that can be embodied in a wide variety of specific contexts. The specific embodiments discussed herein are merely illustrative of specific ways to make and use the invention and do not delimit the scope of the invention.

To facilitate the understanding of this invention, a number of terms are defined below. Terms defined herein have meanings as commonly understood by a person of ordinary skill in the areas relevant to the present invention. Terms such as "a", "an" and "the" are not intended to refer to only a singular entity, but include the general class of which a specific example may be used for illustration. The terminology herein is used to describe specific embodiments of the invention, but their usage does not delimit the invention, except as outlined in the claims.

The present invention describes the biochemical activities of metallo-salen and the development novel anti-tumor agents. The inventors synthesized 45 different derivatives of Mn(III)-salen and Fe(III)-salen with different substituents and bridging spacer groups in the salen ligand and analyzed their apoptotic activities toward different cancer (breast and colon) and normal cells (breast epithelial cells). The results demonstrated that several Mn(III)- and Fe(III)-salen derivatives affect cell viability and induced strong apoptotic activities toward breast cancer cells MCF-7. Treatment with biochemically active Mn(III)- and Fe(III)-salen derivatives for 24 hrs resulted in nuclear condensation (intense DAPI staining), fragmentation and ultimately death in MCF-7 cells. The nuclear condensation and fragmentation are indications of apoptotic pathway of cell death. Moreover, each of these active compounds induced release of cytochrome c from the mitochondria to cytosol suggesting the involvement of mitochondrial pathway of apoptosis.

The present invention analyzed and describes the biochemical and antitumor activities of metallo-salen complexes in cancer cells. Notably, metallo-salens, due to their diverse electronic and structural features show varying spectrum of chemical reactivities and have been extensively used for catalyzing organic reactions[24]. Metallo-salens are also very well studied class of chemical nucleases that bind, cleave, and damage nucleic acids[25-32]. Iron and copper based metallo-salen complexes has been shown to produce reactive oxygen species under reducing environment that damage DNA in a sequence neutral fashion in vitro and have been applied for studying drug-DNA interaction and foot-printing[32,33]. Mn(III)-salen complexes are shown to posses superoxide dismutase (SOD) and catalase activities and are considered as synthetic SOD mimics[34,35]. Recent studies by the present inventors have demonstrated that Fe(III)-salen induces apoptosis in human embryonic kidney (HEK293) cells[36].

Apoptosis is a highly orchestrated cell suicidal program required to maintain a balance between cell proliferation and death. Apoptosis is usually induced by a variety of physiological and external stimuli[1]. Most of the anticancer agents irrespective of their mechanism of action induce apoptosis in cancer cells. Cis-diaminodichloro-platinum(II) (cisplatin) and cis-diamine (cyclobutane-1,1-dicarboxylato) platinum (II) (carboplatin) are the first transition metal based antitumor drugs in clinical use[2-8], Since then many other transition metal complexes as well as small molecule based antitumor agents have been developed and are in clinical trial[2,9-23]. While the platinum based antitumor agents have enormous impact on current cancer therapy, the types of cancer that can be treated with platinum agents are narrow and suffer from side effects and resistance phenomena[7,20]. In order to overcome clinical problems associated with the relatively limited activity of platinum based agents against the broad spectrum of human malignancies, acquired resistance, and side effects, novel non-platinum metal-based anticancer complexes have been and are being developed[20].

Recent advances in understanding the biochemical roles of metal ions and metal complexes and their medicinal application demonstrated significant prospects for the development of metal complexes as drugs[3,10,14,16,17,19,21,32,45-60]. The anticancer and anti-metastatic properties of platinum and ruthenium complexes have been well established and many of these metal-complexes are under intensive pre-clinical and clinical investigations[3]. However, in spite of their great activities toward certain types of cancers cells, many of these metal-complexes are toxic to normal tissues[20]. In addition, several types of cancer cells are resistant to those compounds. Therefore understanding biochemical effects of new and known molecules and developing new biochemically active molecules inducing apoptosis in cancer cells is important for discovering effective anticancer drugs[20].

Herein, in order to explore the biochemical activities of metallo-salen and also to develop novel anti-tumor agents, we synthesized 45 different derivatives of Mn(III)-salen and Fe(III)-salen with different substituents and bridging spacer groups in the salen ligand and analyzed their apoptotic activities toward different cancer (breast and colon) and normal cells (breast epithelial cells). Our results demonstrated that several Mn(III)- and Fe(III)-salen derivatives affect cell viability and induced strong apoptotic activity toward breast cancer cells MCF-7. Treatment with biochemically active Mn(III)- and Fe(III)-salen derivatives for 24 hrs resulted in nuclear condensation (intense DAPI staining), fragmentation and ultimately death in MCF-7 cells. The nuclear condensation and fragmentation are indications of apoptotic pathway of cell death. Moreover, each of these active compounds induced release of cytochrome c from the mitochondria to cytosol suggesting the involvement of mitochondrial pathway of apoptosis.

The nature of the substitutents, bridging spacers and also the central metal-ion played key roles in determining the apoptotic activities and efficiencies of the metallo-salen derivatives of the present invention. The changes in the ethylenediamine bridge to o-phenylene diamine or o naphthalene diamine increased efficiencies of the apoptotic activities of both the Mn(III)- and Fe(III)-salen derivatives of the present invention due to the enhanced interaction between more aromatic salen complexes with DNA. In general, the methoxy substituted metallo-salens were more active than hydroxy substituted metallo-salens with some exceptions. This is attributed to the enhanced permeability through cell membrane. The increase in spacer from ethylenediamine to 1,4-diaminobutane in the salen ligand diminished the apoptosis activity of Fe(III)-salen. The changes in spacing between the diimino group of the salen ligand, increased the flexibility of the metallo-salen complex from nearly planer structure (of Fe(III)-salen) to non-planer three dimensional structure that may perturb physical interaction with nucleic acids and proteins which may have been reflected in the apoptotic activity[61].

The $IC_{50}$ values for the active Mn(III)-salen complexes of the present invention ranged from 12 to 55 µM and Fe(III)-salen complexes 220 nM to 22 µM towards the MCF7 cells, respectively. Most importantly, most of the active Mn(III)-salen derivatives showed 2-5 five fold selectivity in killing cancer cells (MCF-7 and CCL228) over normal cells (breast epithelial cells MCF-10) providing further proof of their potential application as novel anti-tumor agents. The nano molar ranges of $IC_{50}$ values for the selective Fe(III)-complexes of the present invention indicate their effectiveness in killing cells. The $IC_{50}$ value for cis-platin in MCF-7 cells is measured to be ~20 µM which suggest that Mn(III)- and Fe(III)- are comparable or even more effective in inducing cell death in vitro.

The inventors also studied the in vivo efficacy of the selected Mn(III)-salen complexes [3,3'-dimethoxy Mn(III)-salen (compound 6), 3,3'-dihydroxy Mn(III)-salphen (compound 9) and 3,3'-dihydroxy Mn(III)-salnaphen (compound 16) using colon cancer xenograft. Application of the compounds 6 and 9 (3,3'-dimethoxy Mn(III)-salen and 3,3'-dihydroxy Mn(III)-salphen respectively) resulted in complete arrest of tumor growth in vivo in colon cancer xenograft. These results demonstrated that compounds 6 and 9 have antitumor activity in vivo.

The present inventors have synthesized several Mn(III)-salen and Fe(III)-salen derivatives (compounds 1-45, FIG. 1) and investigated their biochemical effects on human breast cancer cells MCF-7, colon cancer cells CCL228 and non-malignant breast epithelial cells MCF-10. We showed that Mn(III)-salen and Fe(III)-salen derivatives affect cell viability and induce apoptosis in MCF-7 cells at nano to micro molar concentration range. Importantly, most of the Mn(III)-salen derivatives and selected Fe(III)-salen derivative exhibited cancer cell selective apoptosis demonstrating their strong potential as novel antitumor agents. Mechanistic studies suggest that metallo-salens induce oxidative stress and activate mitochondrial pathway of apoptosis.

Reagents and Chemicals: All reagents for organic synthesis and buffers were purchased from Sigma-Aldrich unless otherwise noted. Tissue culture medium DMEM (Dulbecco's Modified Eagle's Medium), FBS (Fetal Bovine Serum), penicillin and streptomycin were purchased from Sigma-Aldrich. Ferric chloride (anhydrous) was purchased from Spectrum Chemical Manufacturing Corporation. Anti-cytochrome-c (monoclonal) antibody was purchased from Upstate Biotech, and FITC conjugated anti-mouse secondary antibody was obtained from Jackson Immunoresearch Laboratory. DAPI (4',6-diamidino-2-phenylindole) and anti-actin (monoclonal) were obtained from Chemicon. MTT (3-(4,5-dimethylthiazolyl-2)-2,5-diphenyltetrazolium bromide) was obtained from Tokyo Chemical Industry Co. MCF-7, MCF-10 and CCL228 cell lines were obtained from ATCC (American Type Culture Collection).

Synthesis of Mn(III)- and Fe(III)-salen and their Derivatives (Compounds. 1-45)

Mn(III)- and Fe(III)-salen derivatives were synthesized and characterized following a general procedure as described previously[33,37,36]. In brief, salen ligands were synthesized by mixing two equivalents of salicylaldehyde (or derivatives) with one equivalent of ethylenediamine in methanol at room temperature that resulted in yellow or orange colored precipitate of respective salens. The precipitate was filtered and washed with cold methanol. Each of the ligand was characterized by NMR and/or elemental analysis. Results are consistent with their structures. In order to analyze the biochemical activities of Mn(III)- and Fe(III)-salen derivatives, the inventors synthesized several salen derivatives by changing the spacer between diimino groups and introducing hydroxy and methoxy substituents in the salen ligand using a general procedure (FIG. 1)[36]. For the synthesis of Mn(III)- and Fe(III)-salen derivatives, the respective salen ligand derivatives were dissolved in methanol and then mixed with equivalent amount of anhydrous Mn(III) acetate or Fe(III) chloride in methanol and heated to 60° C. with continuous stirring for 30 min. This resulted in a dark brown/black solution that was cooled down to room temperature. In most cases the metal-complexes were precipitated out upon cooling the reaction mixtures. In some cases the metal complexes were precipitated by adding diethyl ether into the cold reaction mixtures. The products were isolated, recrystallized from methanol characterized and analyzed by NMR and/or elemental analysis and corresponding Mn(III)- and Fe(III)-salen metal complexes were characterized by mass spectrometry (ESI-MS) and/or elemental analysis and the results are consistent with the proposed structures.

Mn(III)-salen acetate (compound 1), Mn(III)-salphen acetate (compound 8) and Mn(III)-salnaphen acetate (compound 15) were synthesized and characterized as described previously[51-53] and Fe(III)-salen chloride (compound 22): These two compounds were synthesized and characterized as previously reported.[36,38]

3,3'-Dihydroxysalen Mn(III) acetate (2): Two equivalents of 2,3-dihydroxybenzaldehyde (1 g, 7.2 mmol) was mixed with one equivalent of ethylenediamine (0.21 g, 3.5 mmol) in methanol that resulted in orange precipitate of 3,3'-dihydroxysalen (L2). L2 (600 mg, 2 mmol) was complexed with one equivalent of Mn(III) acetate (562 mg, 2.1 mmol) to obtain compound 2 (40% yield). Observed m/z value for 3,3'-dihydroxysalen Mn(II) acetate: 353.27 (M+, —OAc); CHN analysis for 3,3'-dihydroxysalen Mn(III) acetate: Calculated (for $C_{18}H_{17}N_2O_6Mn$. $1.0H_2O$) C: 50.24%, H, 4.50%, N, 6.50%. Observed: C: 50.52%, H, 4.76%, N, 6.34%.

4,4'-Dihydroxysalen Mn(III) acetate (3): Two equivalents of 2,4-dihydroxybenzaldehyde (1.38 g, 10 mmol) was mixed with one equivalent of ethylenediamine (0.3 g, 5 mmol) in methanol that resulted in light orange precipitate of 4,4'-dihydroxysalen (L3). This ligand (600 mg, 2 mmol) was complexed with one equivalent of Mn(III) acetate (562 mg, 2 mmol) to obtain compound 3 (45% yield). Observed m/z value for 4,4'-Dihydroxysalen Mn(III) acetate: 353.27 (M+, —OAc). CHN analysis: Calculated (for $C_{18}H_{17}N_2O_6Mn$. $1.0H2O$) C: 50.24%, H, 4.50%, N, 6.50%. Observed: C: 50.48%, H, 4.6%, N, 6.43%.

5,5'-Dihydroxysalen Mn(III) acetate (4): Two equivalents of 2,5-dihydroxybenzaldehyde (1.38 g, 10 mmol) was mixed with one equivalent of ethylenediamine (0.3 g, 5 mmol) in methanol that resulted in reddish brown precipitate of 5,5'-dihydroxysalen (L4). This ligand (600 mg, 2 mmol) was complexed with one equivalent of Mn(III) acetate (562 mg, 2 mmol) to obtain compound 4 (45% yield). Observed m/z value for 5,5'-Dihydroxysalen Mn(III) acetate: 353.27 (M+, —OAc). CHN analysis: Calculated (for $C_{18}H_{17}N_2O_6Mn$. $0.4H_2O$) C: 51.53%, H, 4.28%, N, 6.64%. Observed: C: 51.52%, H, 4.53%, N, 6.82%.

3,3'-Dimethoxysalen Mn(III) acetate (5): Two equivalents of 2-hydroxy-3-methoxybenzaldehyde (1.52 g, 10 mmol) was mixed with one equivalent of ethylenediamine (0.3 g, 5 mmol) in methanol that resulted in bright yellow precipitate of 3,3'-dimethoxysalen ligand (L5). This ligand (656 mg, 2 mmol) was complexed with one equivalent of Mn(III) acetate (562 mg, 2 mmol) to obtain compound. 5 (58% yield). Observed m/z value for 3,3'-Dimethoxysalen Mn(III) acetate: 381.20 (M+, —OAc). CHN analysis: Calculated (for $C_{20}H_{21}N_2O_6Mn$. $3.0H_2O$) C: 48.59%, H, 5.51%, N, 5.66%. Observed: C: 48.77%, H, 5.61%, N, 5.54%.

4,4'-Dimethoxysalen Mn(III) acetate (6): Two equivalents of 2-hydroxy-4-methoxybenzaldehyde (1.52 g, 10 mmol) was mixed with one equivalent of ethylenediamine (0.3 g, 5 mmol) in methanol that resulted in orange brown precipitate of 4,4'-dimethoxysalen ligand (L6). This ligand (656 mg, 2 mmol) was complexed with one equivalent of Mn(III) acetate (562 mg, 2 mmol) to obtain compound. 6 (52% yield). Observed m/z value 4,4'-Dimethoxysalen Mn(III) acetate: 381.20 (M+, —OAc). CHN analysis: Calculated (for $C_{20}H_{21}N_2O_6Mn$. $1.0H_2O$) C: 52.41%, H, 5.06%, N, 6.11%. Observed: C: 52.52%, H, 5.24%, N, 6.15%.

5,5'-Dimethoxysalen Mn(III) acetate (7): Two equivalents of 2-hydroxy-5-methoxybenzaldehyde (1.52 g, 10 mmol) was mixed with one equivalent of ethylenediamine (0.3 g, 5 mmol) in methanol that resulted in bright yellow precipitate of 5,5'-dimethoxysalen (L7). This ligand (656 mg, 2 mmol) was complexed with one equivalent of Mn(III) acetate (562 mg, 2 mmol) to obtain compound. 7 (45% yield). Observed m/z value for 5,5'-Dimethoxysalen Mn(II) acetate: 381.20 (M+, —OAc). CHN analysis: Calculated (for C20H21N2O6Mn. 0.4 H2O) C: 53.67%, H, 4.91%, N, 6.26%. Observed: C: 53.65%, H, 5.06%, N, 6.07%.

3,3'-Dihydroxysalphen Mn(III) acetate (9): Two equivalents of 2,3-dihydroxybenzaldehyde (1.38 g, 10 mmol) was mixed with one equivalent of o-phenylenediamine (540 mg, 5 mmol) in methanol that resulted in red colored precipitate of 3,3'-dihydroxysalphen (L9). This ligand (700 mg, 2 mmol) was complexed with one equivalent of Mn(III) acetate (562 mg, 2 mmol) to obtain compound. 9 (55% yield). Observed m/z for 3,3'-Dihydroxysalphen Mn(III) acetate: 401.27 (M+, —OAc). CHN analysis: Calculated (for $C_{22}H_{17}N_2O_6Mn$. $2.7H_2O$) C, 51.92%, H, 4.43%, N, 5.50%. Observed: C: 51.73%, H, 4.60%, N, 5.55%.

4,4'-Dihydroxysalphen Mn(III) acetate (10): Two equivalents of 2,4-dihydroxybenzaldehyde (1.38 g, 10 mmol) was mixed with one equivalent of o-phenylenediamine (540 mg, 5 mmol) in methanol that resulted in dark orange red precipitate of 4,4'-dihydroxysalen (L10). This ligand (700 mg, 2 mmol) was complexed with one equivalent of Mn(III) acetate (562 mg, 2 mmol) to obtain compound. 10 (60% yield). Observed m/z for 4,4'-dihydroxysalphen Mn(III) acetate: 401.27 (M+, —OAc). CHN analysis: Calculated (for $C_{22}H_{17}N_2O_6Mn$. $1.5H_2O$) C, 54.22%, H, 4.14%, N, 5.80%. Observed: C: 53.97%, H, 4.50%, N, 5.53%.

5,5'-Dihydroxysalphen Mn(III) acetate (11): Two equivalents of 2,5-dihydroxybenzaldehyde (1.38 g, 10 mmol) was mixed with one equivalent of ophenylenediamine (540 mg, 5 mmol) in methanol that resulted in dark reddish brown precipitate of 5,5'-dihydroxysalphen (L11). This ligand (700 mg, 2 mmol) was complexed with one equivalent of Mn(III) acetate (562 mg, 2 mmol) to obtain compound. 11 (45% yield). Observed m/z for 5,5'-dihydroxysalphen Mn(III)

acetate: 401.33 (M+, —OAc). CHN analysis: Calculated (for $C_{22}H_{17}N_2O_6Mn \cdot 2.5H_2O$) C, 52.29%, H, 4.35%, N, 5.54%. Observed: C: 52.43%, H, 4.12%, N, 5.43%.

3,3'-Dimethoxysalphen Mn(III) acetate (12): Two equivalents of 2-hydroxy-3-methoxybenzaldehyde (1.52 g, 10 mmol) was mixed with one equivalent of o-phenylenediamine (540 mg, 5 mmol) in methanol that resulted in bright orange red precipitate of 3,3'-dimethoxysalen ligand (L12). This ligand (752 mg, 2 mmol) was complexed with one equivalent of Mn(III) acetate (562 mg, 2 mmol) to obtain compound 12 (62% yield). Observed m/z for 3,3'-dimethoxysalphen Mn(III) acetate: 429.20 (M+, —OAc). CHN analysis: Calculated (for $C_{24}H_{21}N_2O_6Mn \cdot 1.6H_2O$) C, 55.73%, H, 4.72%, N, 5.41%. Observed: C: 55.38%, H, 4.95%, N, 5.12%.

4,4'-Dimethoxysalphen Mn(III) acetate (13): Two equivalents of 2-hydroxy-4-methoxybenzaldehyde (1.52 g, 10 mmol) was mixed with one equivalent of o-phenylenediamine (540 mg, 5 mmol) in methanol that resulted in bright orange precipitate of 4,4'-dimethoxysalen ligand (L13). This ligand (752 mg, 2 mmol) was complexed with one equivalent of Mn(III) acetate (562 mg, 2 mmol) to obtain compound 13 (58% yield). Observed m/z for 4,4'-dimethoxysalphen Mn(III) acetate: 429.20 (M+, —OAc). CHN analysis: Calculated (for $C_{24}H_{21}N_2O_6Mn \cdot 1.2H_2O$) C, 56.52%, H, 4.62%, N, 5.49%. Observed: C: 56.22%, H, 4.49%, N, 5.25%.

5,5'-Dimethoxysalphen Mn(III) acetate (14): Two equivalents of 2-hydroxy-5-methoxybenzaldehyde (1.52 g, 10 mmol) was mixed with one equivalent of o-phenylenediamine (540 mg, 5 mmol) in methanol that resulted in light red precipitate of 5,5'-dimethoxysalen (L14). This ligand (752 mg, 2 mmol) was complexed with one equivalent of Mn(III) acetate (562 mg, 2 mmol) to obtain compound 14 (50% yield). Observed m/z for 5,5'-dimethoxysalphen Mn(III) acetate: 429.20 (M+, —OAc). CHN analysis: Calculated (for $C_{24}H_{21}N_2O_6Mn \cdot 0.5H_2O$) C, 57.96%, H, 4.46%, N, 5.63%. Observed: C: 58.39%, H, 4.51%, N, 5.56%.

3,3'-Dihydroxysalnaphen Mn(III) acetate (compound 16): Two equivalents of 2,3-dihydroxybenzaldehyde (2.1 g, 15.2 mmol) was mixed with one equivalent of 2,3-diaminonaphthalene (1.1 g, 6.9 mmol) in methanol that resulted in red precipitate of 3,3'-dihydroxysalen (compound L16). This ligand was complexed with one equivalent of Mn(III) acetate to obtain compound 16. Observed m/z for 3,3'-Dihydroxysalnaphen Mn(III) acetate: 451.33 (M+, —OAc). CHN analysis: Calculated (for $C_{26}H_{19}N_2O_6Mn \cdot 3.0H_2O$) C: 55.33%, H, 4.46%, N, 4.96%. Observed: C: 55.44%, H, 4.35%, N, 4.65%.

4,4'-Dihydroxysalnaphen Mn(III) acetate (compound 17). Two equivalents of 2,4-dihydroxybenzaldehyde (1.8 g, 13 mmol) was mixed with one equivalent of 2,3-diaminonaphthalene (1 g, 6.3 mmol) in methanol that resulted in dark orange brown precipitate of 4,4'-dihydroxysalen (L17). This ligand (L17) was complexed with one equivalent of Mn(III) acetate to obtain compound 17. Observed m/z for 4,4'-Dihydroxysalnaphen Mn(III) acetate: 451.33 (M+, —OAc). CHN analysis: Calculated (for $C_{26}H_{19}N_2O_6Mn \cdot 1.5H_2O$) C: 58.11%, H, 4.13%, N, 5.21%. Observed: C: 58.41%, H, 3.89%, N, 5.00%.

5,5'-Dihydroxysalnaphen Mn(III) acetate (compound 18). Two equivalents of 2,5-dihydroxybenzaldehyde (2 g, 14.5 mmol) was mixed with one equivalent of 2,3-diaminonaphthalene (1.1 g, 6.9 mmol) in methanol that resulted in dark red precipitate of 5,5'-dihydroxysalen (L18). This ligand (L17) was complexed with one equivalent of Mn(III) acetate to obtain compound 18. Observed M/Z value for 5,5'-dihydroxy salnaphen Mn(III) acetate: 451.33 (M+, —OAc). CHN analysis: Calculated (for $C_{26}H_{19}N_2O_6Mn \cdot 2.2H_2O$) C: 56.77%, H, 4.23%, N, 5.09%. Observed: C: 56.98%, H, 4.05%, N, 5.31%.

3,3'-Dimethoxysalnaphen Mn(III) acetate (compound 19). Two equivalents of 2-hydroxy-3-methoxybenzaldehyde (2.7 g, 17.5 mmol) was mixed with one equivalent of 2,3-diaminonaphthalene (1.2 g, 7.6 mmol) in methanol that resulted in bright orange precipitate of 3,3'-dimethoxysalen ligand (L19). This ligand (L19) was complexed with one equivalent of Mn(III) acetate to obtain compound 19. Observed M/Z value for 3,3'-dimethoxy salnaphen Mn(III) acetate: 479.27 (M+, —OAc). CHN analysis: Calculated (for $C_{28}H_{23}N_2O_6Mn \cdot 0.5H_2O$) C: 61.43%, H, 4.42%, N, 5.11%. Observed: C: 61.14%, H, 4.78%, N, 5.35%.

4,4'-Dimethoxysalnaphen Mn(III) acetate (compound 20). Two equivalents of 2-hydroxy-4-methoxybenzaldehyde (2.1 g, 13.8 mmol) was mixed with one equivalent of 2,3-diaminonaphthalene (1 g, 6.3 mmol) in methanol that resulted in orange colored precipitate of 4,4'-dimethoxysalen (L20). This ligand (L20) was complexed with one equivalent of Mn(III) acetate to obtain compound 20. Observed m/z value for 4,4'-dimethoxy salnaphen Mn(III) acetate: 479.27 (M+, —OAc). CHN analysis Calculated (for $C_{28}H_{23}N_2O_6Mn \cdot 4.0H_2O$) C: 55.09%, H, 5.12%, N, 4.59%. Observed: C: 54.56%, H, 4.59%, N, 4.86%.

5,5'-Dimethoxysalnaphen Mn(III) acetate (compound 21). Two equivalents of 2-hydroxy-5-methoxybenzaldehyde (2.89 g, 19 mmol) was mixed with one equivalent of 2,3-diaminonaphthalene (1.5 g, 9.5 mmol) in methanol that resulted in dark reddish brown precipitate of 5,5'-dimethoxysalen (L21). This ligand (L21) was complexed with one equivalent of Mn(III) acetate to obtain compound 21. Observed m/z value for 5,5'-dimethoxy salnaphen Mn(III) acetate: 479.27 (M+, —OAc). CHN analysis: Calculated (for $C_{28}H_{23}N_2O_6Mn \cdot 1.2H_2O$) C: 60.05%, H, 4.57%, N, 5.00%. Observed: C: 60.04%, H, 4.56%, N, 5.35%.

3,3'-Dihydroxysalen Fe(III) chloride (compound 23): The ligand 3,3'-dihydroxysalen (L2) was complexed with one equivalent Fe(III) chloride to obtain compound 23. Observed m/z value for 3,3'-Dihydroxysalen Fe(III) chloride (compound 23): 354.20 (M+, —Cl). CHN analysis: Calculated (for $C_{16}H_{14}N_2O_4FeCl \cdot 1.5H_2O$) C: 46.13%, H, 4.11%, N, 6.72%. Observed: C: 46.32%, H, 4.22%, N, 6.85%.

4,4'-Dihydroxysalen Fe(III) chloride (compound 24): The ligand 4,4'-dihydroxysalen (L3) was complexed with one equivalent of Fe(III) chloride to obtain compound 24. Observed m/z value for 4,4'-dihydroxysalen Fe(III) chloride: 354.20 (M+, —Cl). CHN analysis: Calculated (for $C_{16}H_{14}N_2O_4FeCl \cdot 0.5H_2O$) C: 48.21%, H, 3.78%, N, 7.03%. Observed: C: 48.11%, H, 4.08%, N, 6.98%.

5,5'-Dihydroxysalen Fe(III) chloride (compound 25): The ligand 5,5'-dihydroxysalen (L4) was complexed with one equivalent Fe(III) chloride to obtain compound 25. Observed m/z value for 5,5'-dihydroxysalen Fe(III) chloride (compound 25): 354.20 (M+, —Cl). CHN analysis: Calculated (for $C_{16}H_{14}N_2O_4FeCl \cdot 2.4H_2O$) C: 44.39%, H, 4.38%, N, 6.47%. Observed: C: 44.16%, H, 4.33%, N, 6.62%.

3,3'-Dimethoxysalen Fe(III) chloride (26): The ligand 3,3'-dimethoxysalen (L5) was complexed with one equivalent Fe(III) chloride to obtain compound 26. Observed m/z: 382.20 (M+, —Cl). CHN analysis (Calculated for $C_{18}H_{18}N_2O_4FeCl$) C: 51.89%, H, 4.35%, N, 6.72%. Observed: C: 52.15%, H, 4.58%, N, 6.93%.

4,4'-Dimethoxysalen Fe(III) chloride (27): The ligand 4,4'-dimethoxysalen (L6) was complexed with one equivalent Fe(III) chloride to obtain compound 27. Observed m/z value: 382.20 (M+, —Cl). CHN analysis (Calculated for $C_{18}H_{18}N_2O_4FeCl \cdot 1.3H_2O$) C: 49.02%, H, 4.71%, N, 6.35%. Observed: C: 48.64%, H, 4.46%, N, 6.81%.

5,5'-Dimethoxysalen Fe(III) chloride (28): The ligand 5,5'-dimethoxysalen (L7) was complexed with one equivalent of Fe(III) chloride to obtain compound 28. Observed m/z value 382.20 ($M^+$, —Cl). CHN analysis: Calculated (for $C_{18}H_{18}N_2O_4FeCl \cdot 0.2H_2O$) C: 51.32%, H, 4.40%, N, 6.65%. Observed: C: 51.06%, H, 4.53%, N, 6.88%.

Fe(III)-salphen.chloride (compound 29). Two equivalents of salicylaldehyde (2.2 g, 18.1 mmol) was mixed with one equivalent of o-phenylenediamine (920 mg, 8.4 mmol) in methanol that resulted in light orange precipitate of salphen ligand (L8). This ligand (500 mg, 1.6 mmol) was complexed with one equivalent of Fe(III) chloride (295 mg, 1.8 mmol) to obtain compound 29 (65% yield). Observed m/z value for compound 29: 370.18 ($M^+$, —Cl). CHN analysis: Calculated (for $C_{20}H_{14}N_2O_2FeCl \cdot 2.5H_2O$) C: 53.37%, H, 4.26%, N, 6.22%. Observed: C: 53.32%, H, 3.88%, N, 6.00%.

3,3'-Dihydroxysalphen Fe(III) chloride (30): The ligand 3,3'-dihydroxysalphen (L9) was complexed with one equivalent Fe(III) chloride to obtain compound 30. CHN analysis for compound 30 Calculated (for $C_{20}H_{14}N_2O_4FeCl \cdot 2.7H_2O$) C, 49.40%, H, 4.02%, N, 5.76%. Observed: C: 49.08%, H, 3.63%, N, 5.76%.

4,4'-Dihydroxysalphen Fe(III) chloride (compound 31): The ligand 4,4'-dihydroxysalen (L10) was complexed with one equivalent Fe(III) chloride to obtain compound 31. CHN analysis for 4,4'-dihydroxysalphen Fe(III) chloride (compound 31) Calculated (for $C_{20}H_{14}N_2O_4FeCl \cdot 1.8H_2O$) C, 51.17%, H, 3.78%, N, 5.97%. Observed: C: 51.53%, H, 4.28%, N, 5.57%.

5,5'-Dihydroxysalphen Fe(III) chloride (compound 32): The ligand 5,5'-dihydroxysalphen (L11) was complexed with one equivalent of Fe(III) chloride to obtain compound 32. CHN analysis for 5,5'-dihydroxysalphen Fe(III) chloride (compound 32) Calculated (for $C_{20}H_{14}N_2O_4FeCl \cdot 1.7H_2O$) C, 51.30%, H, 3.75%, N, 5.98%. Observed: C: 51.28%, H, 3.77%, N, 5.62%.

3,3'-Dimethoxysalphen Fe(III) chloride (compound 33): The ligand 3,3'-dimethoxysalen (L12) was complexed with one equivalent Fe(III) chloride to obtain compound 33. CHN analysis for 3,3'-dimethoxysalphen Fe(III) chloride (compound 33) Calculated (for $C_{22}H_{18}N_2O_4FeCl \cdot 3H_2O$) C, 50.89%, H, 4.66%, N, 5.39%. Observed: C: 50.63%, H, 4.0%, N, 5.28%.

4,4'-Dimethoxysalphen Fe(III) chloride (compound 34): The ligand 4,4'-dimethoxysalen (L13) was complexed with one equivalent Fe(III) chloride to obtain compound 34. CHN analysis for 4,4'-dimethoxysalphen Fe(III) chloride (compound 34) Calculated (for $C_{22}H_{18}N_2O_4FeCl$) C, 56.74%, H, 3.89%, N, 6.01%. Observed: C: 56.62%, H, 4.04%, N, 6.02%.

5,5'-Dimethoxysalphen Fe(III) chloride (compound 35): The ligand 5,5'-dimethoxysalen (L14) was complexed with one equivalent of Fe(III) chloride to obtain compound 35. CHN analysis 35: Calculated (for $C_{22}H_{18}N_2O_4FeCl$) C, 56.74%, H, 3.89%, N, 6.01%. Observed: C: 56.2%, H, 4.08%, N, 5.93%.

Fe(III)-salnaphen chloride (compound 36): Two equivalents of salicylaldehyde (2.1 g, 17.2 mmol) was mixed with one equivalent of 2,3-diaminonaphthalene (1.3 g, 8.2 mmol) in methanol that resulted in dark yellowish orange precipitate of Salnaphen (L15). This ligand (450 mg, 1.23 mmol) was complexed with one equivalent of Fe(III) chloride (226 mg, 1.4 mmol) to obtain 36 (60% yield). Observed M/Z value for compound 36: 420.24 ($M^+$, —Cl); CHN analysis for 36: Calculated (for $C_{24}H_{16}N_2O_2FeCl \cdot 1.5H_2O$) C: 59.80%, H, 3.97%, N, 5.81%. Observed: C: 60.05%, H, 3.96%, N, 5.78%.

3,3'-Dihydroxysalnaphen Fe(III) chloride (compound 37): The ligands 3,3'-dihydroxysalen (L16, 300 mg, 0.75 mmol) was complexed with one equivalent of Fe(III) chloride (138 mg, 0.85 mmol) to obtain compound 37 (45% yield). Observed m/z value for compound 37: 452.27 ($M^+$, —Cl). CHN analysis: Calculated (for $C_{24}H_{16}N_2O_4FeCl \cdot 2H_2O$) C: 55.04%, H, 3.85%, N, 5.35%. Observed: C: 55.42%, H, 3.59%, N, 5.36%.

4,4'-Dihydroxysalnaphen Fe(III) chloride (compound 38): The ligand 4,4'-dihydroxysalen (L17, 450 mg, 1.3 mmol) was complexed with one equivalent of Fe(III) chloride (243 mg, 1.5 mmol) to obtain compound 38 (48% yield). Observed m/z value for compound 38: 452.27 ($M^+$, —Cl). CHN analysis: Calculated (for $C_{24}H_{16}N_2O_4FeCl \cdot 4H_2O$) C: 51.50%, H, 4.32%, N, 5.00%. Observed: C: 51.10%, H, 4.04%, N, 4.96%.

5,5'-Dihydroxysalnaphen Fe(III) chloride (compound 39): The ligand 5,5'-dihydroxysalen (L18, 450 mg, 1.36 mmol) was complexed with one equivalent of Fe(III) chloride (235 mg, 1.4 mmol) to obtain compound 39 (52% yield). Observed m/z value for compound 39: 452.27 ($M^+$, —Cl). CHN analysis: Calculated (for $C_{24}H_{16}N_2O_4FeCl \cdot 3.5H_2O$) C: 52.35%, H, 4.21%, N, 5.09%. Observed: C: 52.70%, H, 4.07%, N, 5.01%.

3,3'-Dimethoxysalnaphen Fe(III) chloride (compound 40): The ligand 3,3'-dimethoxysalen ligand (L19, 410 mg, 0.96 mmol) was complexed with one equivalent of Fe(III) (186 mg, 1.15 mmol) chloride to obtain compound 40 (65% yield). Observed m/z value for compound 40: 480.18 ($M^+$, —Cl). CHN analysis: Calculated (for $C_{26}H_{20}N_2O_4FeCl \cdot 3.8H_2O$) C: 53.45%, H, 4.76%, N, 4.80%. Observed: C: 53.27%, H, 3.95%, N, 4.93%.

4,4'-Dimethoxysalnaphen Fe(III) chloride (compound 41): The ligand 4,4'-dimethoxysalen (L20, 450 mg, 1.1 mmol) was complexed with one equivalent of Fe(III) chloride (194 mg, 1.2 mmol) to obtain compound 8 (58% yield). Observed m/z value for compound 41: 480.25 ($M^+$, —Cl). CHN analysis: Calculated (for $C_{26}H_{20}N_2O_4FeCl \cdot 1.0H_2O$) C: 58.51%, H, 4.15%, N, 5.25%. Observed: C: 58.43%, H, 3.80%, N, 5.27%. 5,5'-Dimethoxysalnaphen Fe(III) chloride (compound 42): The ligand 5,5'-dimethoxysalen (L21, 400 mg, 0.94 mmol) was complexed with one equivalent of Fe(III) chloride (192 mg, 1.2 mmol) to obtain compound 42 (59% yield). Observed m/z value for compound 42: 480.18 ($M^+$, —Cl). CHN analysis: Calculated (for $C_{26}H_{20}N_2O_4FeCl$) C: 60.55%, H, 3.91%, N, 5.43%. Observed: C: 60.07%, H, 3.73%, N, 5.44%.

Bis(salicylidene)propanediamine Fe(III) chloride (43):Bis (salicylidene) propanediamine ligand was prepared by mixing two equivalent of salicylaldehyde with 1 equivalent of 1,3-diaminobutane in methanol that resulted in greenish yellow precipitate of bis(salicylidene)propane diamine that was complexed with 1 equivalent of Fe(III) chloride to obtain compound 43. MS (ESI-MS) for Bis(salicylidene)propanediamine Fe(III) chloride: 336.27 ($M^+$, —Cl).

Bis(salicylidene)butanediamine Fe(III) chloride (44): Bis (salicylidene)butanediamine ligand was prepared by mixing two equivalent of salicylaldehyde with 1 equivalent of 1,4-diaminobutane in methanol that resulted in yellow precipitate of bis(salicylidene)butanediamine that was complexed with 1 equivalent of Fe(III) chloride to obtain compound 44. MS (ESI-MS) for Bis(salicylidene)butanediamine Fe(III) chloride: 350.20 ($M^+$, —Cl).

Fe(III)-carboxysalphen] chloride (compound 45). Two equivalents of salicylaldehyde was mixed with one equivalent of 3,4-diaminobenzoic acid in methanol that resulted in orange colored precipitate of caboxysalphen that was complexed with one equivalent of Fe(III) chloride to obtain compound 45. CHN analysis for compound 45: Calculated (for $C_{21}H_{14}N_2O_4FeCl. 1.0 H_2O$) C: 54.01%, H, 3.24%, N, 6.00%. Observed: C: 53.83%, H, 3.48%, N, 5.95%.

Cell culture: Monolayer of human breast cancer cells (MCF-7), colon cancer (CCL228) and breast epithelial cell (MCF-10) were grown and maintained in Dulbecco's modified Eagle's media (DMEM) that was supplemented with heat inactivated fetal bovine serum (FBS, 10%), L-glutamine (1%) and Penicillin/streptomycin (0.1%)[39-41]. Cells were cultured and maintained in humidified incubator with 5% $CO_2$ in air at 37° C. Cells were grown on cover slips for microscopy studies and in 96 well micro titer plates for cell viability and cytotoxicity assays.

Cell viability assay: Approximately 10,000 MCF-7 cells were seeded into each well of a 96 well micro titer plate and incubated 24 hrs in presence of 150 µL DMEM. An additional 50 µL DMEM containing required amount of each metallo-salen to obtain 20 µM final concentrations (in 200 µL final volume) in 8 replicate wells were added. Control wells were treated with equivalent amount of dimethylsulfoxide (DMSO). The viability of the cells was assayed at 24, 48, 72 and 96 hrs post treatment by using both microscopic observation and MTT assay. For microscopic observation cells were stained with trypan blue for at least 10 minute and observed under Differential Interference Contrast (DIC) setting of a fluorescence microscope (Nikon Eclipse TE2000-U, Japan). The MTT assay was performed as described previously[42]. In brief, 20 µL MTT (5 mg/ml in PBS) was added into each wells and incubated for 2 hrs under normal growth condition to allow the viable cell to convert MTT to formazan. Then the media was discarded and formazan crystals were dissolved by adding 100 µL of DMSO and incubating 2 hrs with continuous shaking. The absorbance of the lysates were directly measured at 560 nm using a micro plate reader (Fluostar-omega, BMG Labtech). The absorbance values (which are proportional to the viable cell) are plotted as a function of time. The studies were repeated twice with 8 replicates each time.

Cytotoxicity assay ($IC_{50}$ measurement): The cytotoxicity of Fe(III)-salen and its derivatives was determined by using MTT assay as described previously[42]. In brief, approximately 10,000 MCF-7 cells were seeded into each well of a 96 well micro titer plate and incubated 24 hrs in presence of 150 µL DMEM. An additional 50 µL DMEM containing required amount of each metallo-salen to obtain 0.05 to 60 µM final concentration (in 200 µL final volume) in 8 replicate wells were added. Control wells were treated with equivalent amount of DMSO. After 96 hrs of incubation, 20 µL of MTT (5 mg/mL) was added into each well and cell viability was assayed by measuring the formazan absorption at 560 nm as described above. The absorbance (at 560 nm) values were plotted against concentration of metallo-salens to determine the $IC_{50}$. The studies were repeated twice with 8 replicates each time.

Nuclear fragmentation with DAPI (4',6-diamidino-2-phenylindole) staining: MCF-7 cells were seeded onto a cover slip in a 60 mm plate and grown overnight under normal growth conditions followed by incubation with 100 µM Fe(III)-salen or its derivatives for additional 24 hrs. Control cells were treated with equivalent amount of DMSO. Cells were fixed with 4%-formaldehyde in PBS for 15 minutes, washed twice with PBS, permeabilized with 0.2% Triton X-100 in PBS for 5 min. Cells were washed three times with cold PBS followed by incubation with DAPI (5 µg per slide) for 10 minutes at room temperature. DAPI stained cells were washed three times with cold PBS, mounted on microscope slide with mounting media (Vectashield H-1000, Vector lab) and visualized under fluorescence microscope[8].

Immuno-staining with anti-cytochrome-c: MCF-7 cells were seeded onto a cover glass for 24 hrs and subjected to immuno-staining with anti-cytochrome-c as described previously[43,44 8]. In briefly, cells were fixed for 10 minutes with 4% formaldehyde, washed twice with PBS, permeabilized for 10 minutes using 0.2% Triton X-100 in PBS. Cells were blocked with 10% goat serum for 1 hr prior to incubation with anti-cytochrome c antibody for additional 1 hr. Cells were washed thrice with 0.02% tween-20 in cold PBS. Secondary antibodies conjugated with FITC were used for immuno-fluorescence detections by incubating for 30 minute. Cells were washed thrice with cold PBS. Nuclear counterstaining was performed with DAPI. Immuno-stained cells were mounted and observed by using fluorescence microscope.

Caspase-3/7 activity assay: Caspase-3/7 activity was assessed using SensoLyte™ Homogenous AMC Caspase-3/7 Assay Kit (AnaSpec Inc). Briefly, cells were treated with 100 µM Fe (III) and Mn(III)-salen complexes separately for 0, 8, 16, and 24 hrs, lysed, and centrifuged (2500 g for 10 min at 4° C.). The supernatant was diluted (to 1 µg/µL of protein) and 150 µL extract was mixed with 50 µL of assay buffer containing caspase-3/7 substrate, incubated for 15 min at 37° C. and then fluorescence intensity ($350_{EX}/440_{EM}$) was measured every 10 min (up to 2 hrs) using FLOUstar Omega micro plate reader (BMG labTech). The concentration of activated caspase-3/7 was calculated by using calibration curve with pure standard. The caspase-3/7 activity was finally expressed relative to untreated control cells.

Application of metallo-salen complexes in colon cancer xenograft.

Figure 8A:
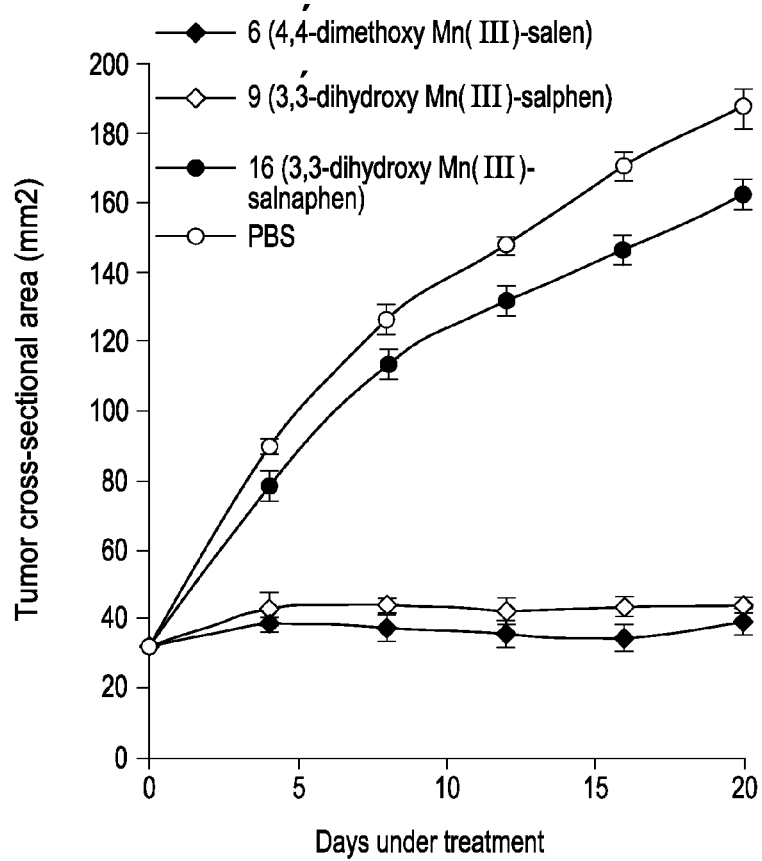
FIG. 8 shows the regression of tumor xenograft by Mn(III)-salen complexes (compounds 6, 9 and 16). Athymic nude nu/nu mice carrying the colon cancer xenograft were administered with 10 mg/kg of 3,3'-dimethoxy Mn(III)-salen (compound 6), 3,3'-dihydroxy Mn(III)-salphen (compound 9) and 3,3'-dihydroxy Mn(III)-salnaphen (compound 16) at 4 days interval, for over a period of 21 days. Tumor diameters were measured using a slide caliper prior to each administration and plotted (left panel). Bar indicated standard deviation (3 replicate experiments). Right panel shows the pictures of the treated and control mouse at different time points.

All the animal experiments were carried out using the IACUC approved protocol. For examining the efficacies of metallo-salen complexes, the inventors administered selected metallo-salen complexes in PBS intraperitoneally on Athymic nude nu/nu mice (Harlan) carrying the colon cancer xenografts. In brief, $2 \times 10^6$ human colon cancer cells (CCL228 cell in 100 µl of PBS) were injected subcutaneously (near the right back limb). Animals were examined daily for signs of tumor growth and behavior. Once the tumor size reached ~25 mm² (2 to 3 weeks after injection of cells) the inventors administered the metallo-salen complexes intraperitoneally (in PBS solution, twice in a week, in three parallel replicates). Control mice were injected with equal volume of the diluents (PBS) alone. Prior to every new treatment with metallo-salen complexes, bi-dimensional measurements were carried out using calipers and cross-sectional area (tumor size) and data were plotted (FIG. 8A).

The inventors studied the effect of Mn(III)-salen and Fe(III)-salen derivatives on the cell viability of cultured breast cancer cells MCF-7 in order to investigate the biochemical effects of the derivatives. The cells were incubated alone or with 20 µM of each of the metallo-salen derivatives separately (compounds 1-45) for varying time periods (0-96 hrs). The viable cells were quantified using MTT assay and the percent of cell survived (relative to the control untreated cells) were plotted against time (FIGS. 2A-2F). The DIC (Differential Interference Contrast) images of cells under light microscope in the absence and presence of each Mn(III)- and Fe(III)-salen derivatives are shown on the right panels (FIGS. 2A'-2F') which shows visual effects of each compounds on MCF-7 cell. The activities of compounds 1-42 on cell viability are summarized in Table 1.

Figure 2A:
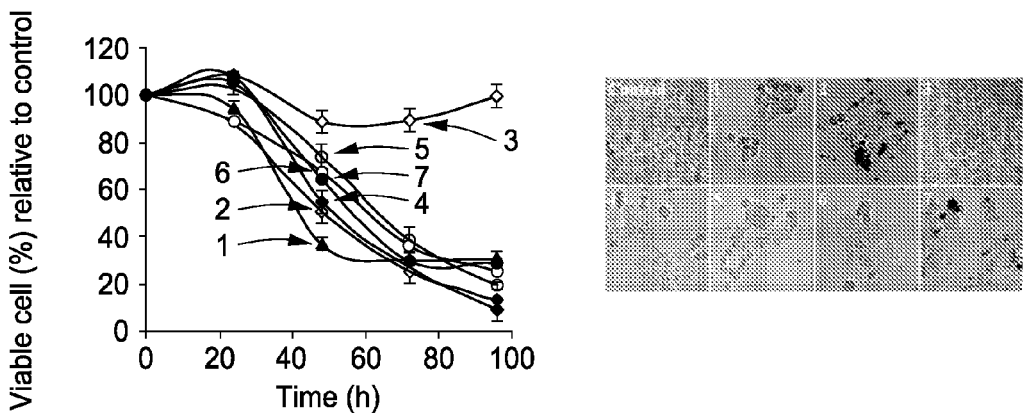
FIG. 2 shows the effect of Mn(III)-salen, Fe(III)-salen and their derivatives on cell viability. (A-F): MCF-7 cells were treated with 20 µM metallo-salens and incubated for varying time periods (24-96 hrs). Viable cells were quantified using MTT assay. The percent viable cells (relative to control, treated with equivalent amount of DMSO) were plotted as a function of time for each compound. This experiment was repeated twice with 8 replicate treatments each time. Bars indicates standard errors of mean (SEM). Curves 1-42 in FIGS. 2A-2F, represent the viability curves for compounds 1-42 respectively. (A'-F') DIC images of the corresponding MCF-7 cells that were treated with DMSO (control panel), or with 20 µM Mn(III)- and Fe(III)-salen complexes for 72 hrs showing the visual effects on cellular morphology and growth/death. Numbers on each panel represent the corresponding complexes as shown in FIG. 1.

In case of Mn(III)-salen and derivatives several compounds showed significant effects on cell viability (FIGS. 2A-2F and Table 1). In the salen series with ethylene diamine bridge, the parent Mn(III)-salen (compound 1), 3,3'- and 5,5'- dihydroxy Mn(III)-salen (compounds 2 and 4), and all the methoxy substituted Mn(III)-salen (3,3'-, 4,4'- and 5,5'-dimethoxy Mn(III)-salen, compounds 5, 6 and 7 respectively) induced significant (40-60%) cell death within 48 hrs post treatment in comparison to the control (FIG. 2A/A'). In most cases, about 80% or more cells were dead by 96 hrs. Interestingly, 4,4'-dihydroxy Mn(III)-salen (compound 3) did not have any significant effect on cell viability which suggest that the position of the substituent on salen ligand play critical role in determining their biochemical activities (FIG. 2A/A' and Table 1). Notably, although, 4,4'-dihydroxy Mn(III)-salen was inactive corresponding 4,4'-dimethoxy Mn(III)-salen (compound 6) induced efficient cell death on MCF-7 cell (FIG. 2A/A' and Table 1).

Change in the bridging group from ethylene diamine to o-phenylene diamine and 2,3-diamino naphthalene (compounds 1, 8 and 15) increased the cytotoxicity of the metallo-salens (24 hrs time points, FIGS. 2A/A', 2B/B' and 2C/C'). Interestingly, the pattern of effects on cell viability of hydroxy/methoxy substituted Mn(III)-salphen derivatives (compounds 8-14) and hydroxy/methoxy substituted Mn(III)-salnaphen derivatives (compounds 15-21) were almost similar to corresponding Mn(III)-salen derivatives (FIGS. 2 A/A', 2B/B' and 2C/C' and Table 1). Notably, 4,4'-dihydroxy Mn(III)-salen and salphen derivatives (compounds 3 and 10) were not active while corresponding 4,4'-dihydroxy Mn(III)-salnaphen (compounds 17) was effective in inducing cell death in MCF-7 cells (FIGS. 2 A/A', 2B/B' and 2C/C' and Table 1).

Similarly, 5,5'-dihydroxy Mn(III)-salen and salphen derivatives (compounds 4 and 11) were effective in inducing cell death while corresponding 4,5'-dihydroxy Mn(III)-salnaphen (compound 18) was inactive (FIGS. 2 A/A', 2B/B' and 2C/C' and Table 1). 4,4'-methoxy Mn(III) salphen, the parent Mn(III)-salnaphen (compounds 13 and 15) were most effective on inducing cell death (FIGS. 2A/A', 2B/B' and 2C/C') by 48 hrs.

Figure 2B:
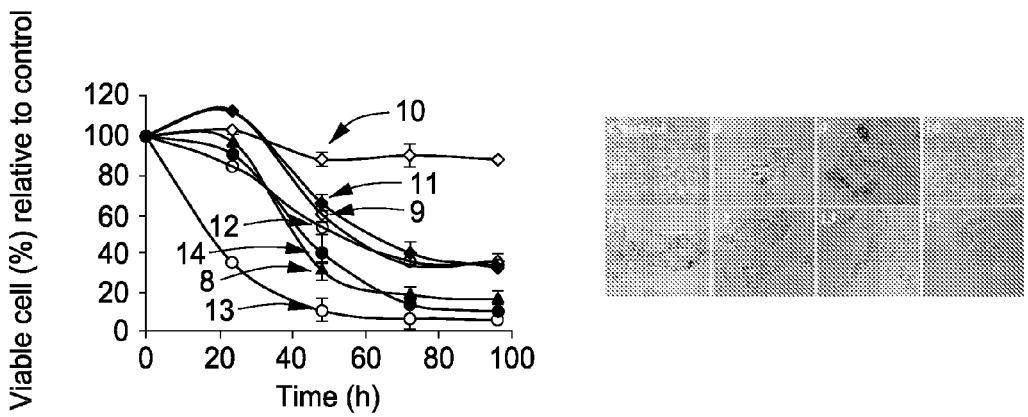
Figure 2C:
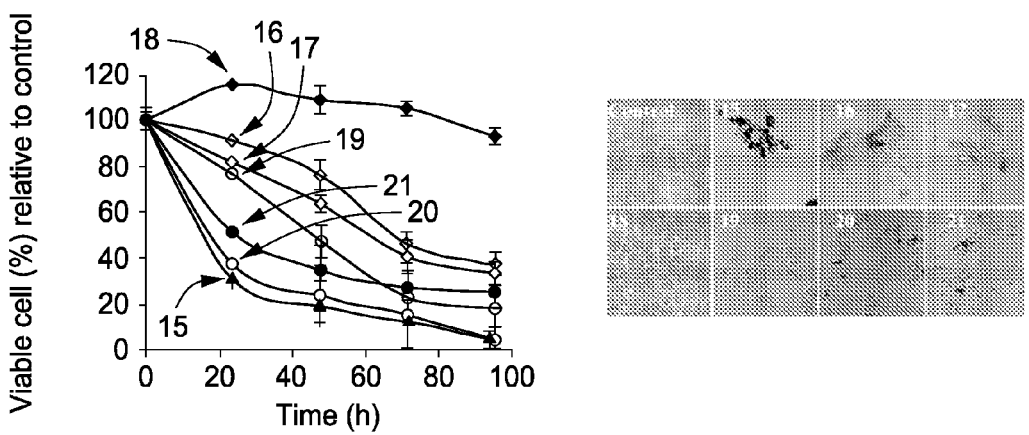
Figure 2D:
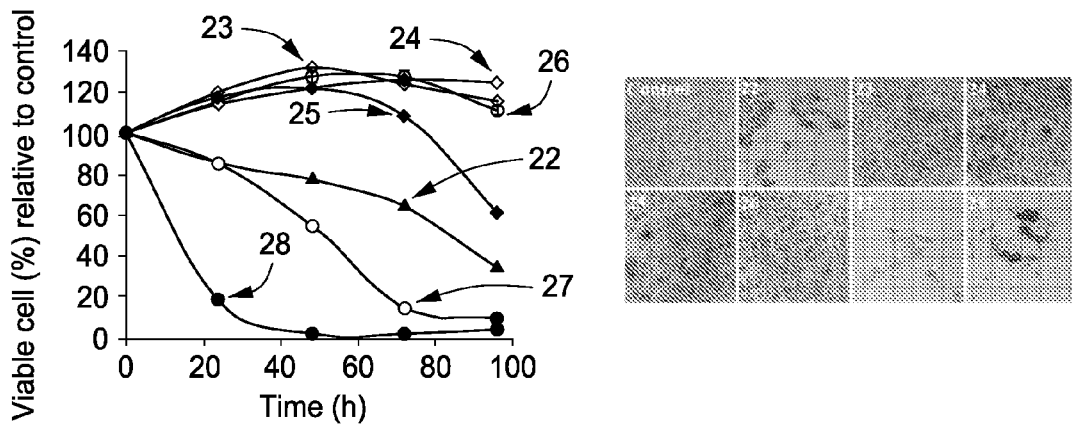
Figure 2E:
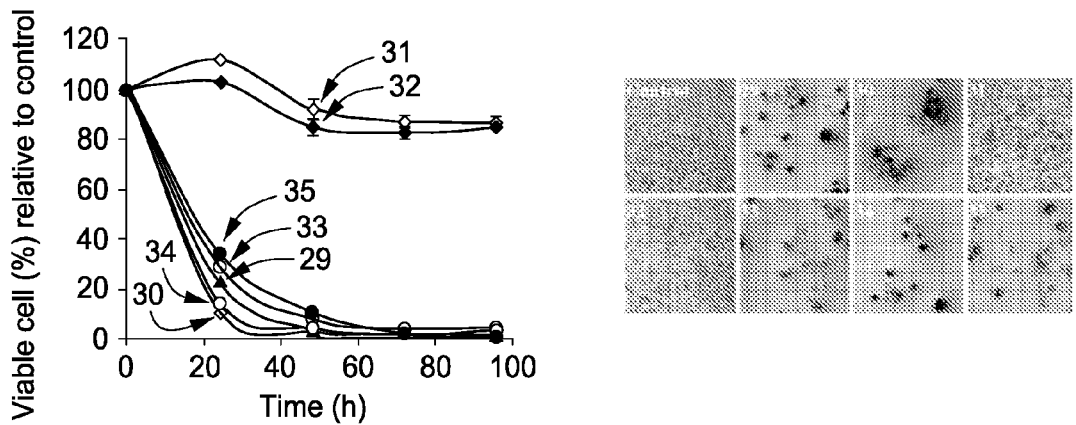
Figure 2F:
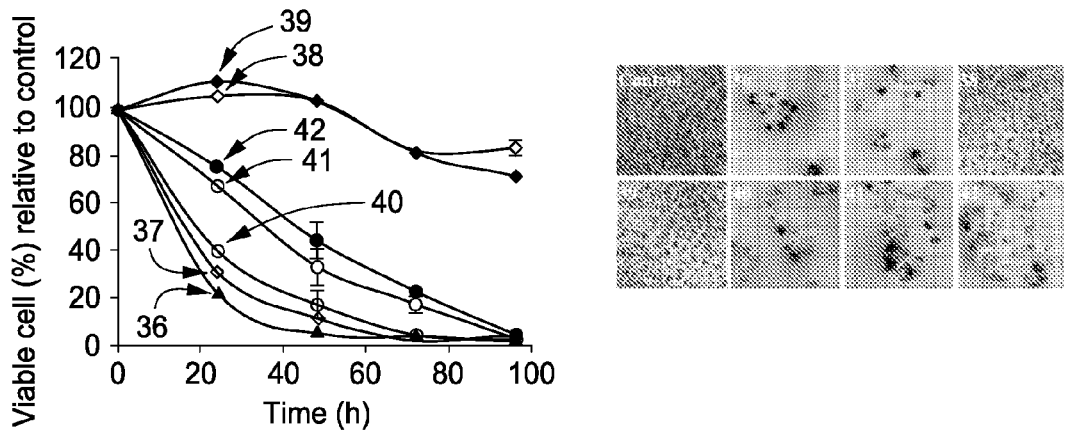

In case of Fe(III)-salen derivatives, the overall pattern of cell killing activity was very different in comparison to Mn(III)-salen derivatives (FIGS. 2A-2C versus FIGS. 2D-2F and Table 1). Among the salen derivatives, only Fe(III)-salen, 4,4'-, and 5,5'-methoxy substituted Fe(III)-salens (compounds 22, 27, and 28, respectively) were highly effective in killing MCF-7 cells in a time dependent manner (FIG. 2D/D'). 5,5'-dimethoxy Fe(III)-salen (compound 28) killed more than 80% of cells in less than 24 hrs, while 4,4'-dimethoxy Fe(III)-salen (compound 27) took about 72 hrs to induce similar extent of cell death (FIG. 2D). In contrast, 3,3'-dimethoxy Fe(III)-salen (compound 26) did not show any significant effect on cell viability (FIG. 2D/D'). Similarly, none of the corresponding hydroxy substituted Fe(III)-salen derivatives (compounds 23-25) killed MCF-7 cells under similar conditions even at 96 hrs of incubation (FIG. 2D/D'). In addition, Fe(III)-salen derivatives with longer spacer between the diimino bridges, compounds 43 and 44, and negatively charged carboxysalphen Fe(III) chloride (compound 45) showed almost no cell killing activity under similar condition (data not shown). In case of Fe(III)-salphen and Fe(III)-salnaphen derivatives, all the methoxy substituted derivatives (compounds 33-35 and 40-42) as well as 3,3'-dihydroxy substituted derivatives (compounds 30 and 37) were very efficient in inducing cell death on MCF-7 cells (FIGS. 2E/E', 2F/F' and Table 1).

4,4'- and 5,5'-hydroxy substituted Fe(III)-salphens and Salnaphens (compounds 31, 32, 38 and 39) did not have any effects on cell viability (FIGS. 2E/E', 2F/F' and Table 1). Thus changing the bridging group from ethylene diamine to o-phenylene diamine and 2,3-diamino naphthalene made a significant difference in terms of reactivities of the methoxy as well as hydroxy substituted Fe(III)-salphen and salnaphen derivatives. These observations are in contrast to the Mn(III) complexes which suggest that not only the substituent but also the nature of the central metal-ion plays a critical role in determining the cell killing activities of metallo-salens.

TABLE 1

Summary of cell viability activities.

| | | Metal Ion | | | | | |
|---|---|---|---|---|---|---|---|
| | | Mn (III) | | | Fe (III) | | |
| | Bridge | En[a] | Phen[a] | Naphen[a] | En | Phen | Naphen |
| Substituent | H | Y[b] (1) | Y (8) | Y (15) | Y (22) | Y (29) | Y (36) |
| | 3,3'-OH | Y (2) | Y (9) | Y (16) | N (23) | Y (30) | Y (37) |
| | 4,4'-OH | N[b] (3) | N (10) | Y (17) | N (24) | N (31) | N (38) |
| | 5,5'-OH | Y (4) | Y (11) | N (18) | N (25) | N (32) | N (39) |
| | 3,3'-OMe | Y (5) | Y (12) | Y (19) | N (26) | Y (33) | Y (40) |
| | 4,4'-OMe | Y (6) | Y (13) | Y (20) | Y (27) | Y (34) | Y (41) |
| | 5,5'-OMe | Y (7) | Y (14) | Y (21) | Y (28) | Y (35) | Y (42) |

[a]En: Ethylene diamine, Phen: ortho-phenylene diamine, Naphen: 2,3-diamino naphthalene.
[b]Y and N indicates active and inactive compounds respectively. The number inside the parenthesis indicates the respective compounds in FIG. 1.

The cytotoxicity of Mn(III)- and Fe(III)-salen derivatives toward MCF-7 cells were quantified by performing MTT assay[36,42] to determine the $IC_{50}$ values as the different Mn(III) and Fe(III)-salen derivatives showed differential effects on cell viability, the inventors incubated the MCF-7 cells (in 96 well tissue culture plates) with varying concentrations of each of the metallo-salens for 96 hrs and then subjected to MTT assay. The concentration of the metal-complexes at which the conversion of MTT to formazan by viable cells is reduced by 50% compared to control cells is defined as the $IC_{50}$. The percent of cell survival relative to the control cells were plotted as a function of concentration of the metallo-salen derivatives.

Figure 3A:
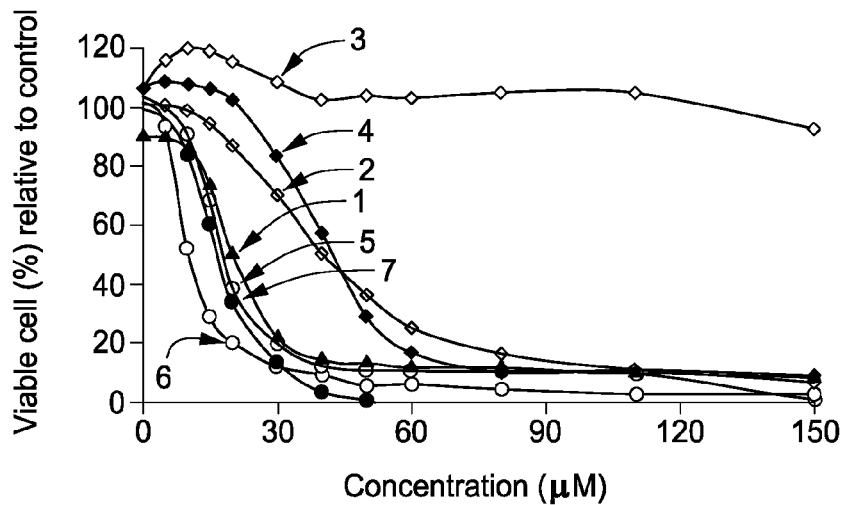
FIG. 3 shows $IC_{50}$ measurements for Mn(III)- and (Fe(III)-salen and their derivatives on MCF-7 cells. Approximately 10,000 cells were grown in each well of a 96 well microtiter plate for 24 hrs and then treated with varying concentrations (0.05 to 60 µM) of metallo-salens for 96 hrs. Viable cells at different concentrations of metallo-salen treatment were quantified using MTT assay. The percent viable cells (relative to control DMSO treated) were plotted against concentration for each compound separately. The concentration of the metal-complexes at which the conversion of MTT to formazan by viable cells is reduced by 50% compared to control cells is defined as the $IC_{50}$ Curves 1-42 in FIGS. 3A-3F represent cytotoxicity curves for corresponding metal complexes 1-42 respectively.
Figure 3B:
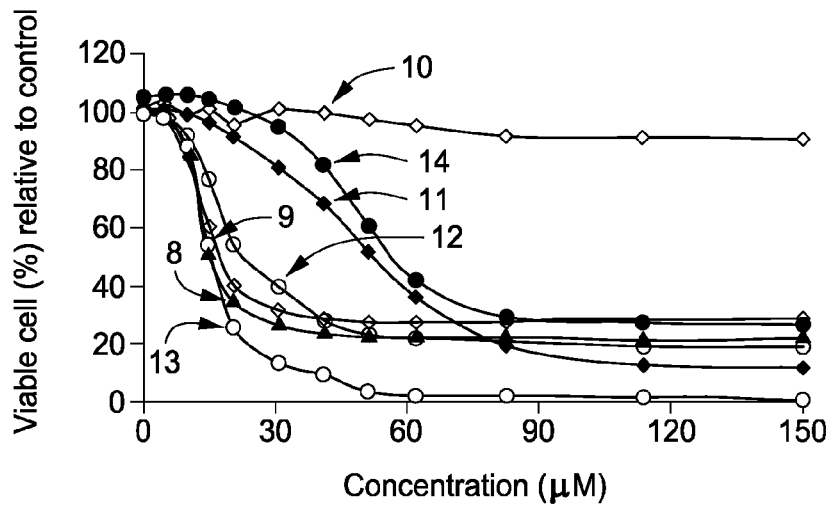
Figure 3C:
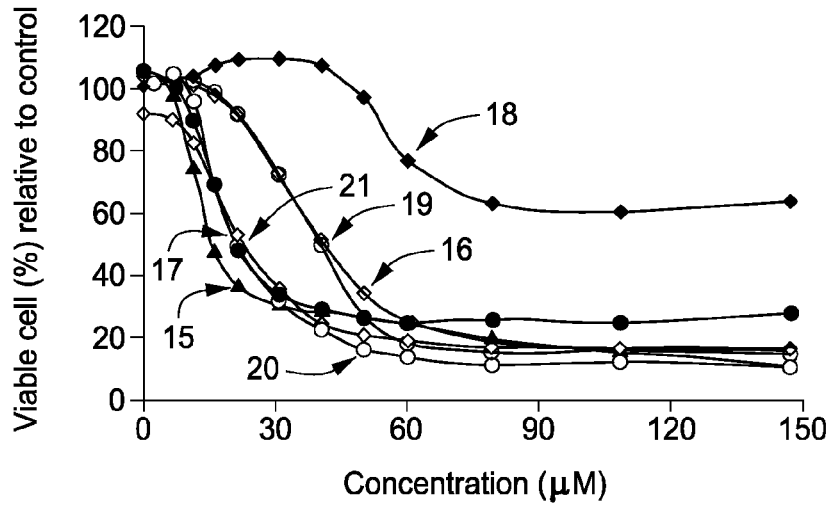

FIGS. 3A-3F represent $IC_{50}$ curves for Mn(III)- and Fe(III)-complexes (compounds 1-42) and the $IC_{50}$ values for each active compounds are summarized in Table 2. $IC_{50}$ values for most of the active Mn(III)-complexes lie between 12 to 23 μM except compounds 2, 4, 11, 14, 16 and 19 whose $IC_{50}$ values were higher than 40 μM (FIGS. 3A-3C and Table 2). Specifically, the parent unsubstituted Mn(III)-salen, salphen and salnaphen (compounds 1, 8 and 15) and 4,4'-dimethoxy substituted Mn(III)-complexes (compounds 6, 13 and 20) were the highly effective with $IC_{50}$ values 20.4, 15.0, 15.5, 12.3, 15.5 and 20.4 µM respectively (Table 2). Similarly, compounds 5 (3,3'-dimethoxy Mn(III)-salen), 7 (5,5'-dimethoxy Mn(III)-salen), 9 (3,3'-dihydroxy Mn(III)-salphen), and 21 (5,5'-dimethoxy Mn(III)-salnaphen) have $IC_{50}$ values below 20 µM (Table 2).

Figure 3D:
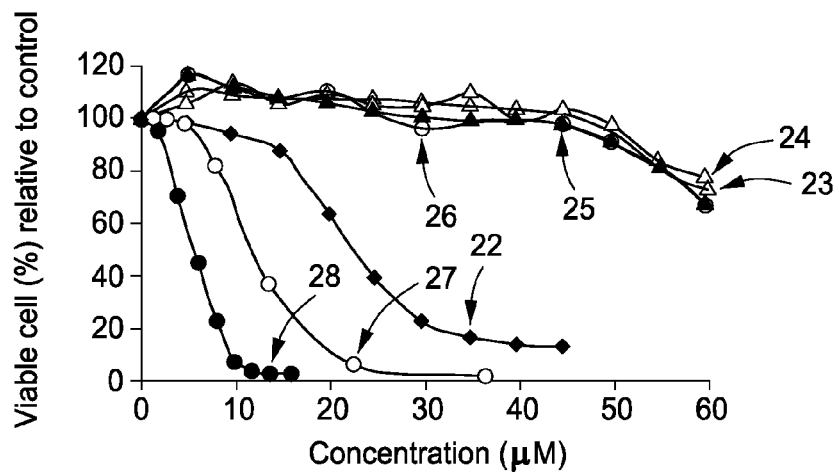
Figure 3E:
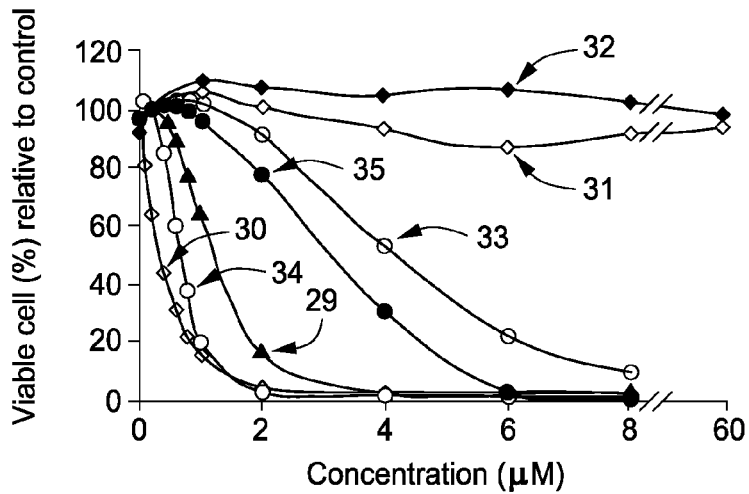
Figure 3F:
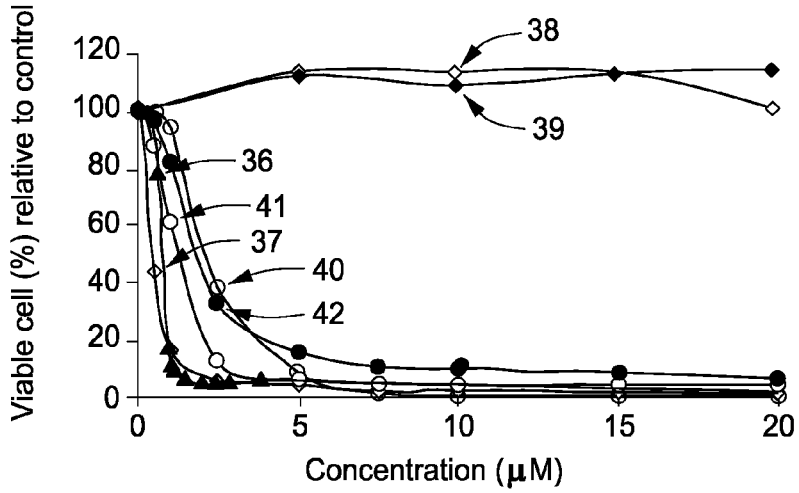

The $IC_{50}$ values for several Fe(III)-complexes were in the nanomolar range which includes 3,3'-dihydroxy Fe(III)-salphen (compound 30, $IC_{50}$: 330 nM), 4,4'-dimethoxy-Fe(III)-salphen (compound 34, $IC_{50}$: 680 nM), Fe(III)-salnaphen (compound 36, $IC_{50}$: 540 nM), 3,3'-dihydroxy Fe(III)-salnaphen (compound 37, $IC_{50}$: 220 nM) and 4,4'-dimethoxy Fe(III)-salnaphen (compound 41, $IC_{50}$: 530 nM) toward MCF-7 cells (Table 2 and FIGS. 3D-3F). Several other Fe(III)-compounds $IC_{50}$ values lay between 1-5 µM. These results indicate that Fe(III)-salen derivatives have high efficiency in inducing cell death in MCF-7 cells and 3,3'-hydroxy and 4,4'-methoxy substituted salphen and salnaphen derivatives are the most potent (Table 2).

antitumor drugs have nano molar $IC_{50}$ values, these compounds have significant potential toward anti-tumor applications.

To study the pathway, by which metallo-salen derivatives of the present invention induce cell death, the inventors analyzed the effects of different metallo-salens on the nuclear integrity by using fluorescent dye DAPI staining. DAPI is a DNA binding dye that has been used extensively for staining cell nucleus. We treated MCF-7 cells with 100 µM of Mn(III)- and Fe(III)-salen and their derivatives and incubated for 24 hrs. Cells were stained with DAPI and visualized under fluorescence microscope.

The results were in agreement with cell viability data, except 4,4'-dihydroxy Mn(III)-salen and salphen and 5,5'-dihydroxy Mn(III)-salnaphen derivatives (compounds 3, 10 and 18), all other remaining Mn(III)-complexes (compounds 1-2, 4-9, 11-17, 19-21) derivatives induced significant morphological changes with more intense DAPI staining, highly condensed and fragmented nucleus in comparison to

TABLE 2

$IC_{50}$ values for different complexes in MCF-7 cells.

| Bridge | | Metal Ion | | | | |
|---|---|---|---|---|---|---|
| | | Mn(III) | | | Fe(III) | |
| | | En[a] | Phen[a] | Naphen[a] | En | Phen | Naphen |
| Substituent | H | (1) 20.48 | (8) 15.02 | (15) 15.56 | (22) 22.45 | (29) 1.25 | (36) 0.54 |
| | 3,3'-OH | (2) 36.95 | (9) 17.26 | (16) 40.28 | N (23) | (30) 0.33 | (37) 0.22 |
| | 4,4'-OH | N (3) | N (10) | (17) 21.38 | N (24) | N (31) | N (38) |
| | 5,5'-OH | (4) 43.13 | (11) 45.6 | N (18) | N (25) | N (32) | N (39) |
| | 3,3'-OMe | (5) 17.73 | (12) 22.18 | (19) 39.72 | N (26) | (33) 4.15 | (40) 1.5 |
| | 4,4'-OMe | (6) 12.31 | (13) 15.56 | (20) 20.48 | (27) 12.4 | (34) 0.68 | (41) 0.53 |
| | 5,5'-OMe | (7) 16.15 | (14) 55.88 | (21) 19.26 | (28) 4.56 | (35) 3.11 | (42) 1.24 |

The number inside the parenthesis indicates the respective compounds in FIG. 1.
[a]En: Ethylene diamine, Phen: ortho-phenylene diamine, Naphen: 2,3-diamino naphthalene.

To study the anti-tumor drug potential of Mn(III)- and Fe(III)-metallo salen derivatives, the inventors analyzed $IC_{50}$ values for the each of the active compounds towards different cancer as well as normal cells. The $IC_{50}$ values for different active compounds (compounds 1-42) for three different cell lines, MCF-7 (breast cancer), CCL228 (colon cancer) and MCF-10 (non malignant breast cells), are plotted in the bar graph in FIG. 4. Interestingly, most of the active Mn(III)-complexes (except compounds 5, 11 and 20) showed significant (2-5 fold) selectivity towards breast and colon cancer cells (MCF-7 and CCL228) over nonmalignant breast epithelial cells (MCF-10). The preferential apoptotic activities toward cancer cells over non cancer cells suggest the strong potential of Mn(III)-salen derivatives toward anti-tumor drug application.

Figure 4A:
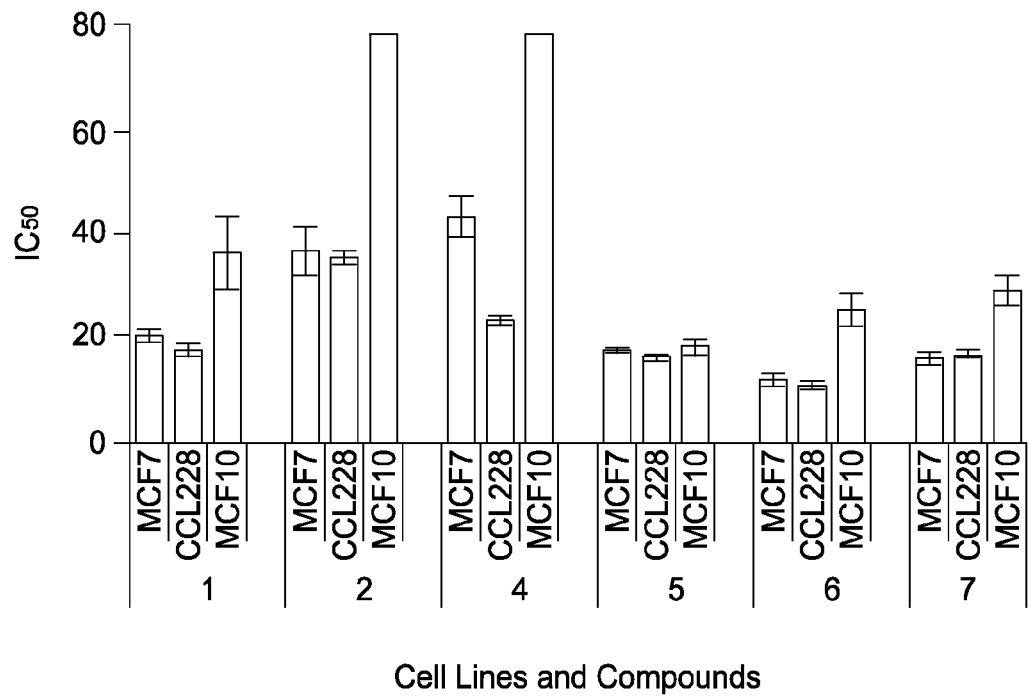
FIG. 4 shows the $IC_{50}$ values for Mn(III)- and Fe(III)-salen derivatives toward different cancer and normal cell lines. $IC_{50}$ values for each biochemically compounds were determined using MTT assay in three different cell lines that include MCF-7 (breast cancer), CCL228 (colon cancer) and MCF-10 (normal breast epithelial cells). $IC_{50}$ values were for comparison for each compound (compounds 1-45) as marked. The results for the inactive compounds are not shown in the figure.
Figure 4B:
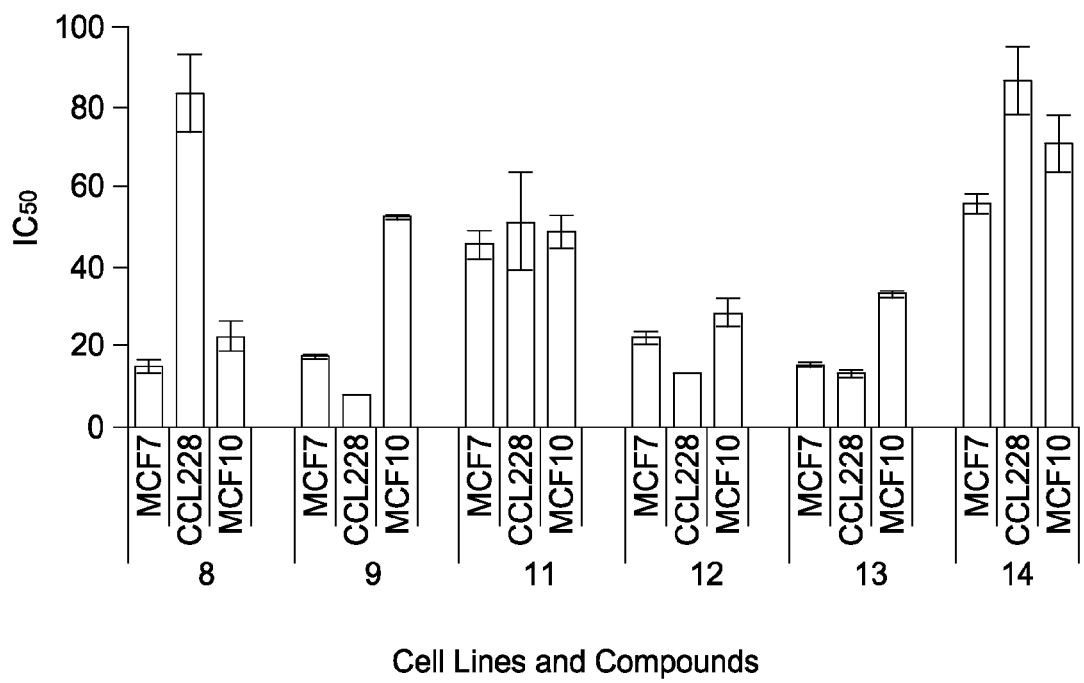
Figure 4C:
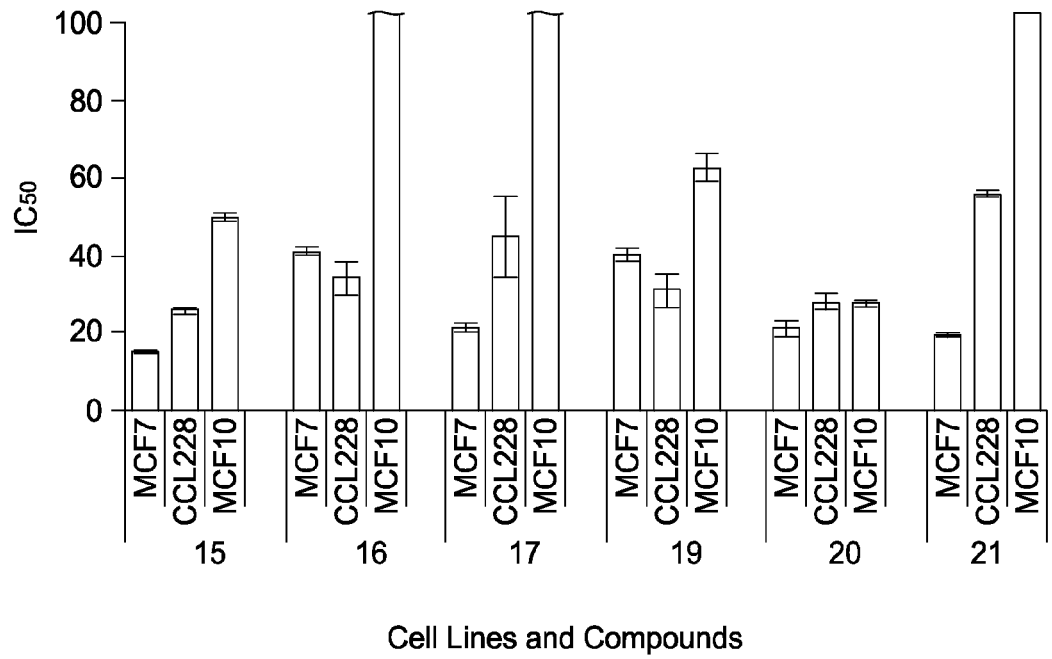
Figure 4D:
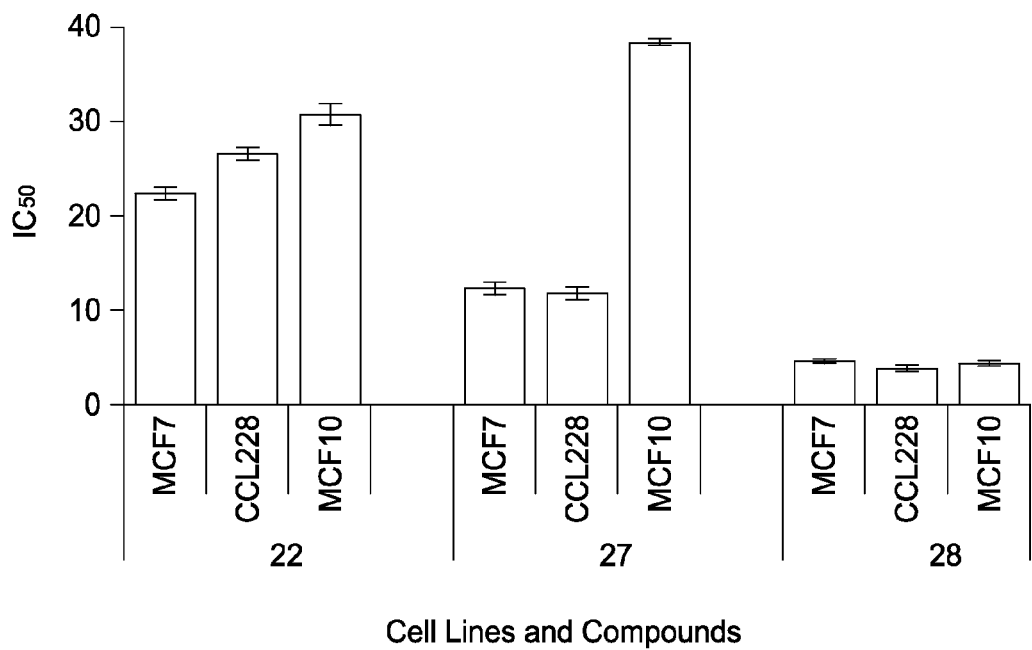
Figure 4E:
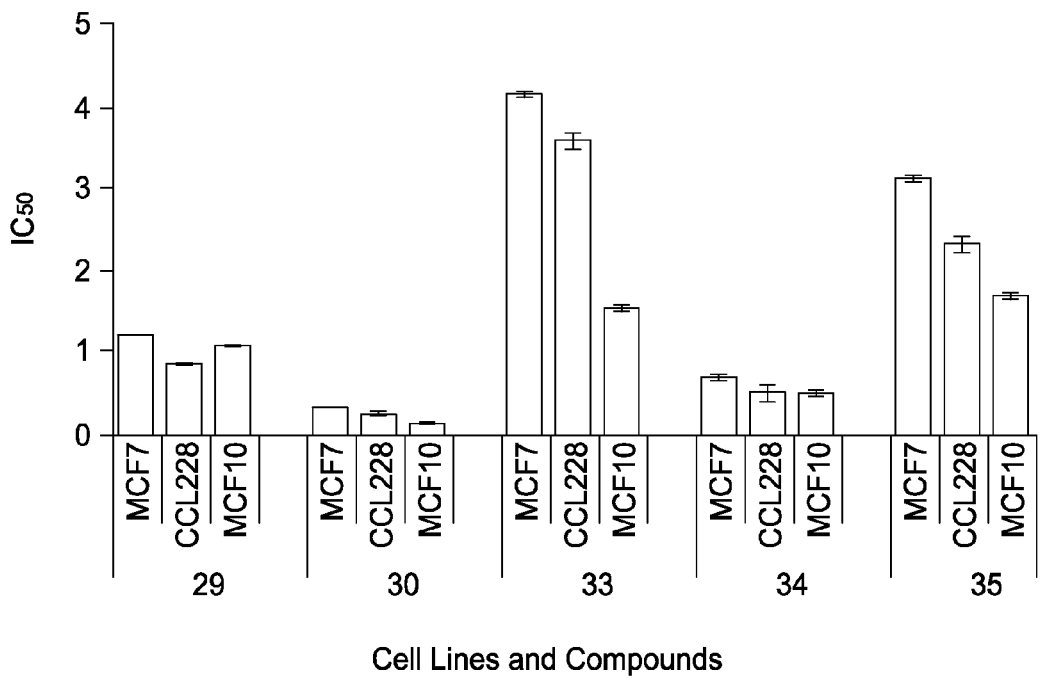
Figure 4F:
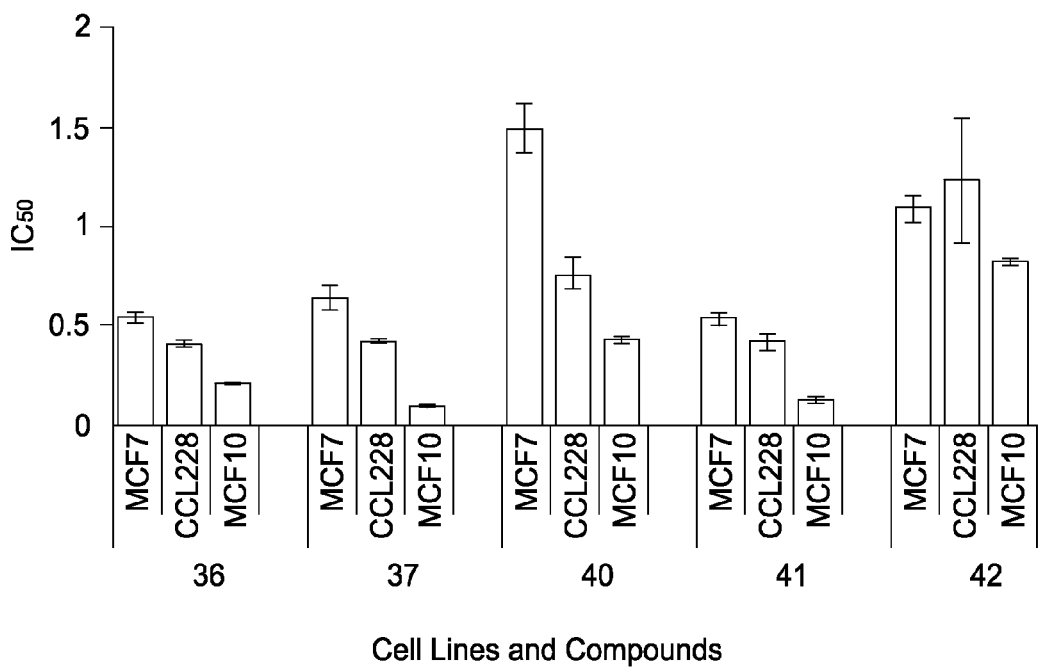
Figure 5A:
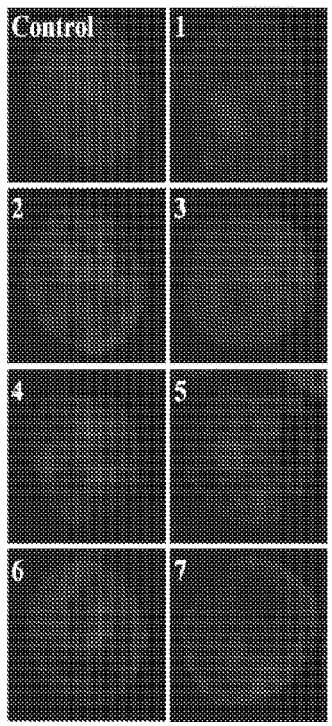
FIG. 5 shows the Effect of Mn(III)- and Fe(III)-salen derivatives on nuclear integrity (DAPI staining). MCF-7 cells, grown on a cover glass in a 60 mm culture plate for 24 hrs, were treated alone or with 100 µM metallo-salens separately for 24 hrs, fixed with formaldehyde, stained with DAPI followed by visualization under fluorescence microscope. Control panel indicates cells that were treated with DMSO. Panels 1-42 represent cells treated with compounds 1-42 respectively.
Figure 5B:
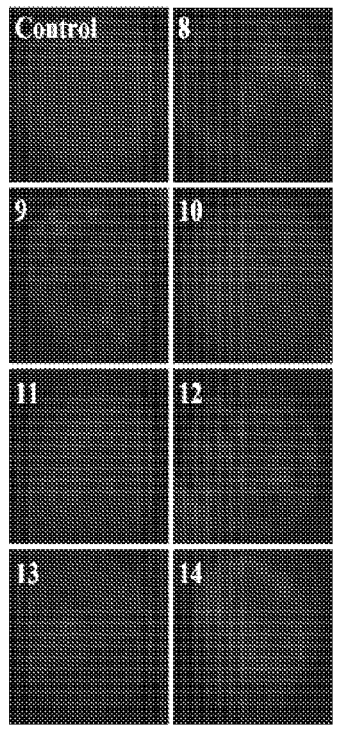
Figure 5C:
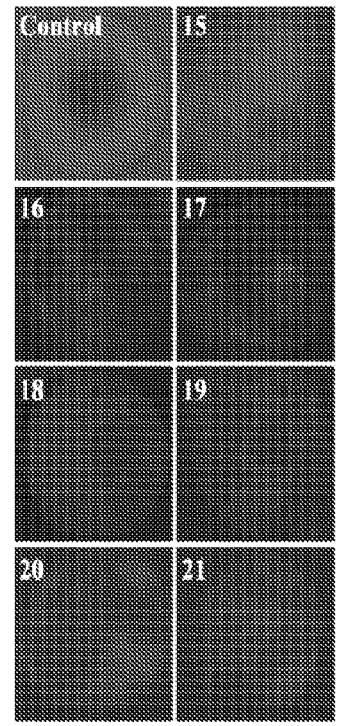

In contrast to Mn(III)-complexes, most of the Fe(III)-salen complexes killed normal cells (MCF-10) more preferentially over cancer cells except compounds 1 and 27 (FIGS. 4D-4F). Compound 27 killed MCF-7 and CCL228 cells about 4 fold more efficiently over MCF-10 non malignant cells (FIG. 4D). These data suggest that compound 27 may have strong potential toward anti-tumor therapeutic application. Notably, as several Fe(III)-complexes (such as compounds 30, 34, 36, 37, and 41) have nano-range of $IC_{50}$ values and many effective untreated control cells (FIGS. 5A, 5B and 5C represent Mn(III)-salen, salphen and salnaphen derivatives respectively). The effects were more severe on some cases in comparison to others likely because of their efficiencies. The nuclear fragmentation and condensation indicates that Mn(III)-salen complexes induced apoptotic cell death in MCF-7 cells.

Figure 5D:
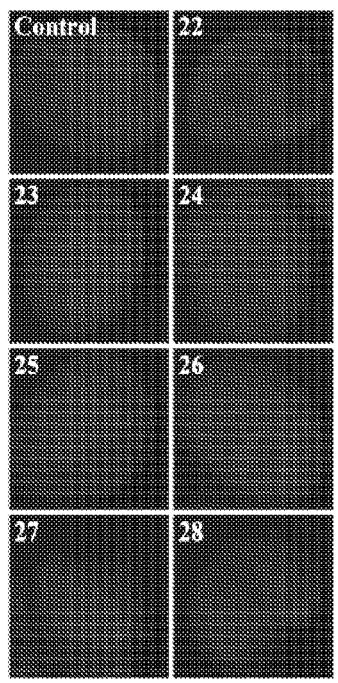
Figure 5E:
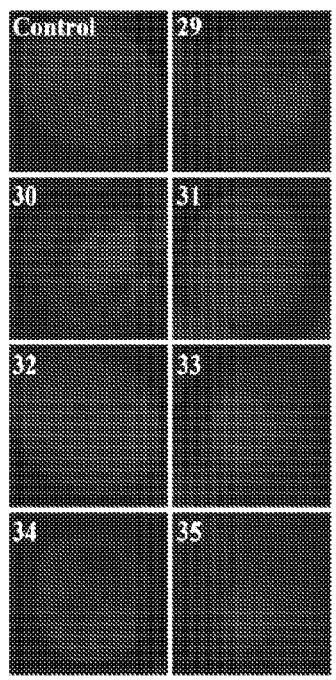
Figure 5F:
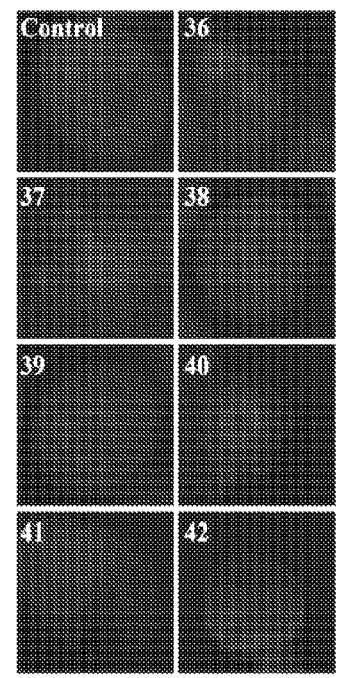
Figure 6A:
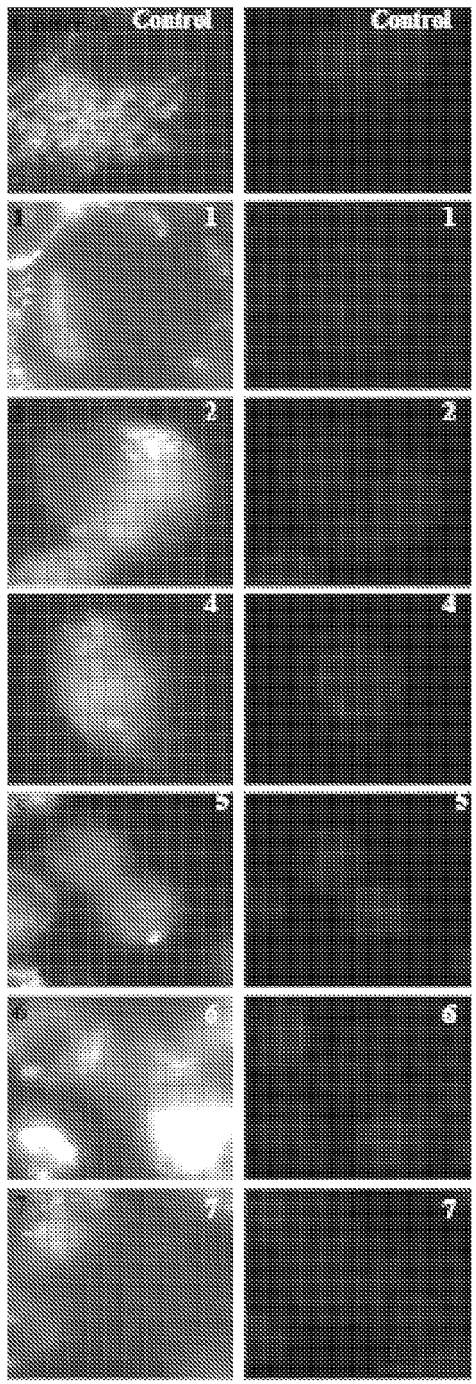
FIG. 6 shows the Cytochrome-c translocation induced by Mn(II)- and Fe(III)-salen derivatives. MCF-7 cells were seeded onto a cover glass for 24 hrs, treated with 100 µM metallo-salens and incubated for additional 16 hrs. Cells were fixed with formaldehyde, immuno-stained with anti-cytochrome c and FITC conjugated secondary antibodies and visualized under fluorescence microscope (left panels). The corresponding cell nucleus was visualized by DAPI staining (right panels). Control panels: cell treated with DMSO; Panels 1-42 represent cells that were treated with compounds 1-42 respectively.
Figure 6B:
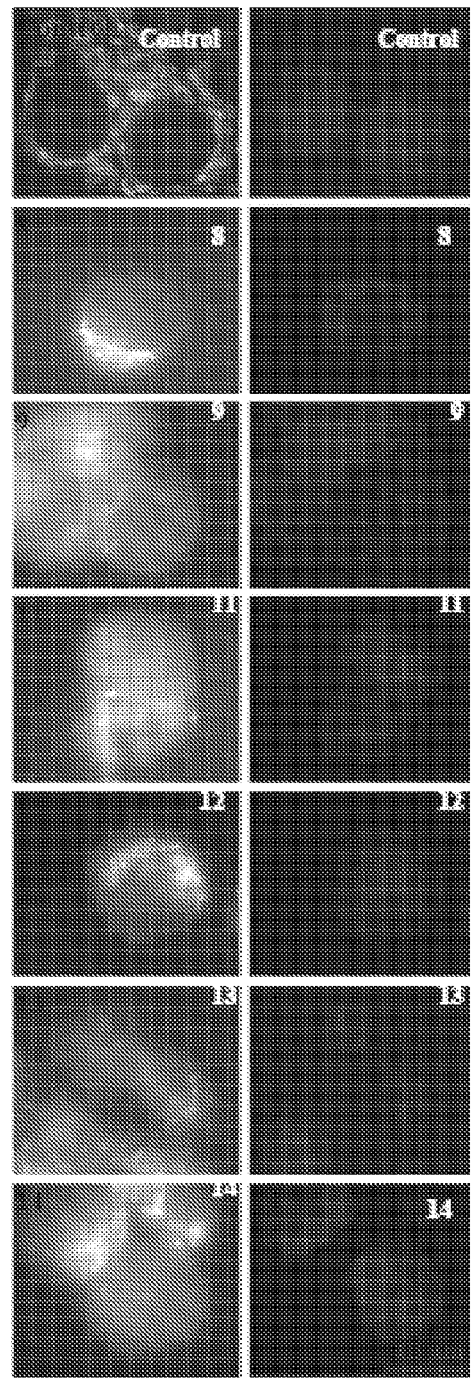
Figure 6C:
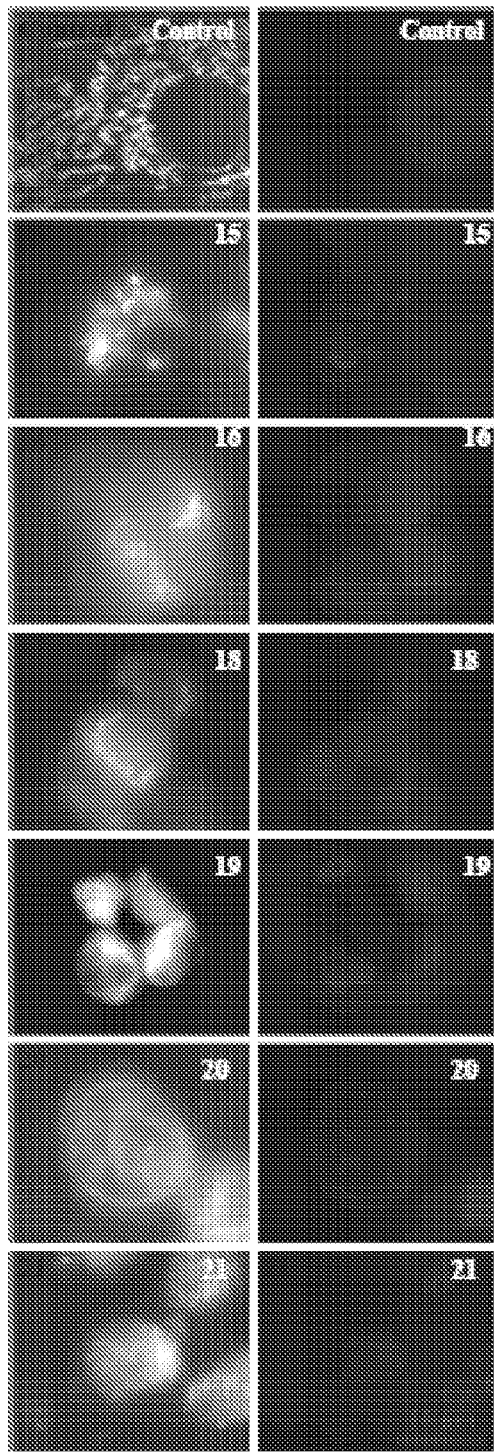
Figure 6D:
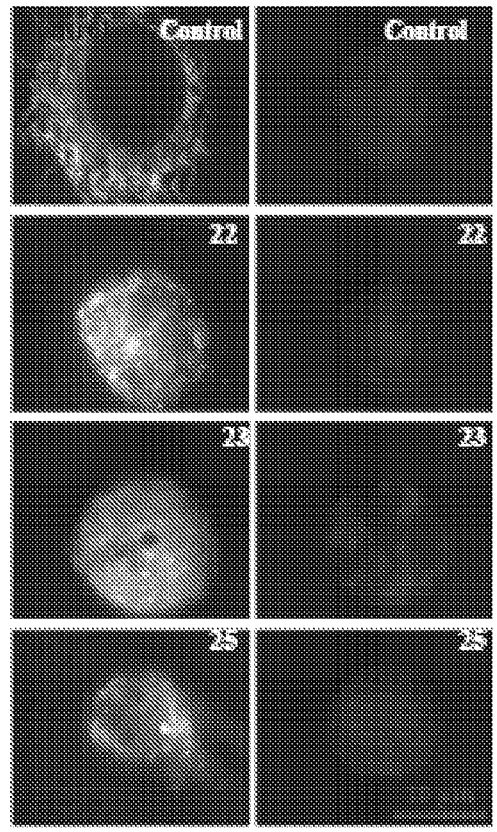
Figure 6E:
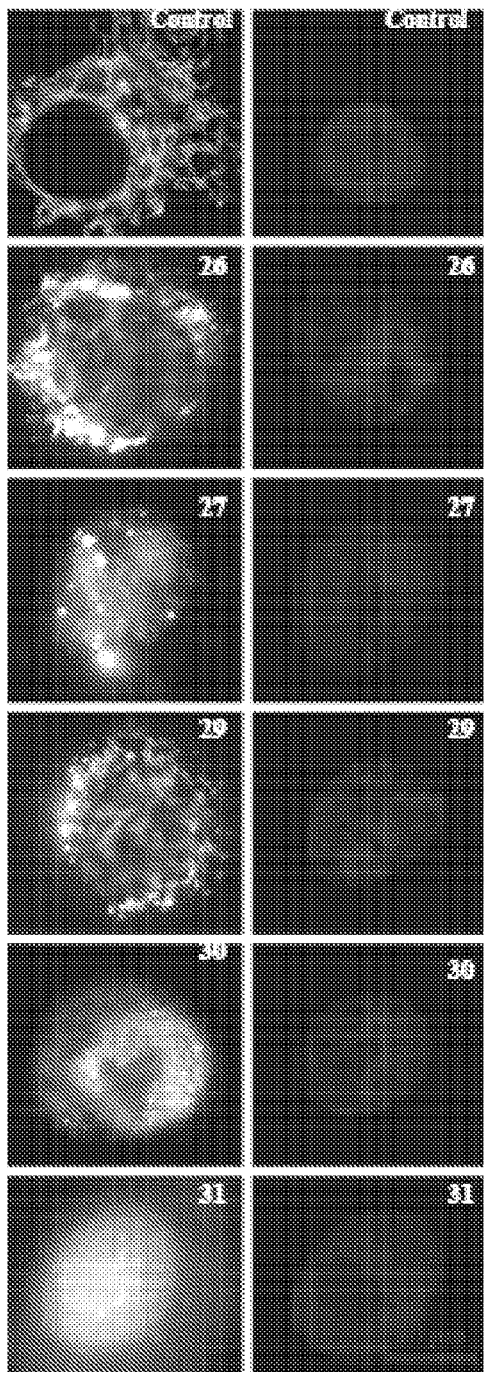
Figure 6F:
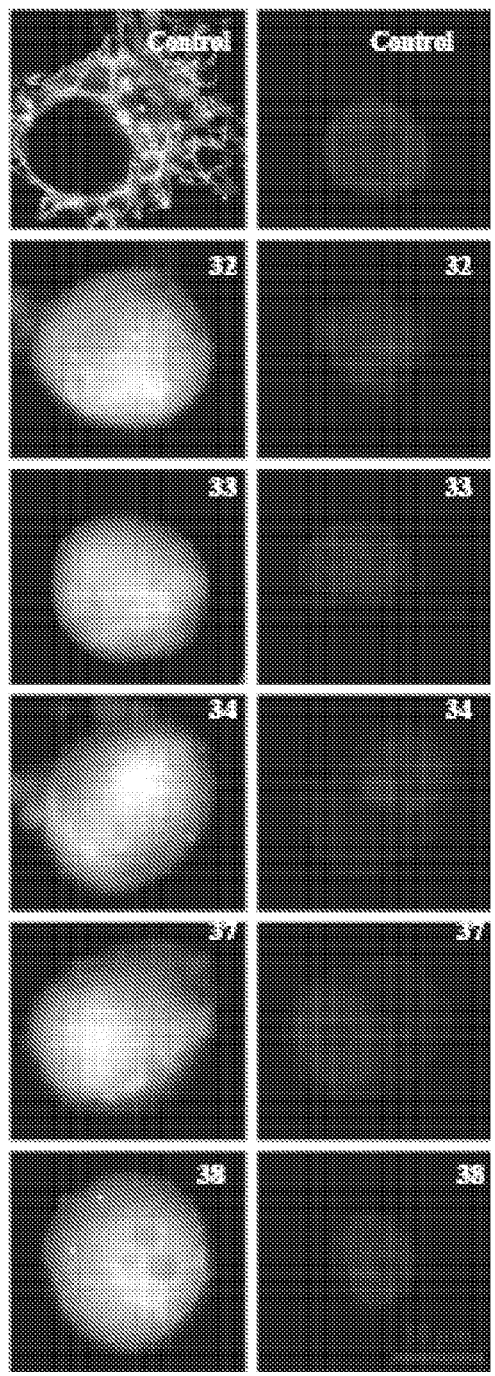

The effects of Fe(III)-salen derivatives (compounds 22-45) on nuclear morphology by DAPI staining is shown in FIGS. 5D-5F. Again, in agreement with cell viability activities, compounds 22, 27-28, 29, 30, 33-35, 36, 37, and 40-42 showed significant effects on nuclear morphology and fragmentation indicating apoptotic cell death.

To understand the pathway by which Mn(III)- and Fe(III)-salen derivatives induced apoptosis in MCF-7 cells, the inventors performed immuno-staining with anti-cytochrome c antibody before and after treatment with Mn(III)- and Fe(III)-salen derivatives [44]. The cytochrome-c immuno-stained cells were visualized under fluorescence microscope (left panels, FIG. 6) and the corresponding cell nucleus was visualized by DAPI staining (right panels, FIG. 6). As expected the cytochrome c is localized inside the mitochondria in control untreated cells as evidenced by the speckles outside the nucleus (top control panels on each of the FIGS.

6A-6F). However, treatment with biochemically active Mn(III)-salen derivatives (FIG. 6A), Mn(III)-salphen derivatives (FIG. 6B), Mn(III)-salnaphen derivatives (FIG. 6C), Fe(III)-salen derivatives (FIG. 6D), Fe(III)-salphen derivatives (FIG. 6E), and Fe(III)-salnaphen derivatives (FIG. 6F) resulted in release of cytochrome c from mitochondria to the cytosol as evidenced by its spreading throughout the cell. In contrast, inactive compounds showed no significant effect on cytochrome c translocation (data not shown). It is well known that cytochrome c is normally present inside the mitochondria and translocate to cytosol upon changes in mitochondrial membrane potential leading to caspase 9 activation during apoptotic process. The release of cytochrome c from the mitochondria to the cytosol suggested that Mn(III)- and Fe(III)-salen derivatives induced apoptosis in MCF-7 cells via mitochondrial pathway.

To further confirm the apoptotic activities of Mn(III) and Fe(III)-salen derivatives of the present invention, the inventors analyzed the activation of caspases-3/7 enzymes. Notably, to assess the caspase 3/7 activity we used CCL228 cells instead of MCF7 as MCF7 cells lack the caspase-3 enzyme[56]. The inventors treated cells with 100 μM of Mn (III)-salen or Fe(III)-salen complexes separately (compounds 1-42) for 0, 8, 16 and 24 h and then analyzed the caspase-3/7 activities by using a commercial caspase-3/7 assay kit. The caspase activities of the cells treated with biochemically active Mn(III) and Fe(III)-salen derivatives were increased with time with a maxima at 16 h post treatment and then declined at higher time points likely due to cell death (data not shown). The relative caspase-3/7 activities (at 16 h time point) of the different metallo-salen derivatives of the present invention in CCL228 cells are plotted in FIG. 7.

Figure 7:
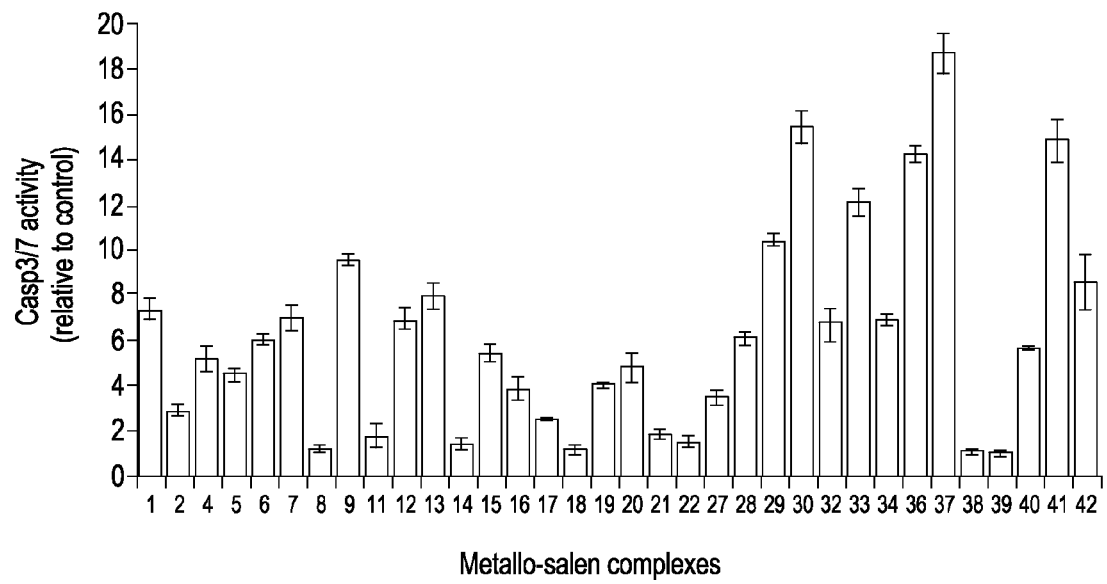
FIG. 7 shows the Mn (III) and Fe(III)-salen derivatives (compounds 1-42) activate caspase-3/7. CCL228 (human colon cancer) cells were treated with 100 µM metallo-salen derivatives for 16 h and subjected to caspase 3/7 activation assay using a commercially available caspase-3/7 Assay Kit (AnaSpec Inc). The relative caspase-3/7 activity (compared to the untreated control) was plotted for different metallo-salen derivatives. Bars indicated SEM.

As CCL228 cells were used for the caspase assay, the inventors compared the caspase activity data of different metallo-salen complexes with their corresponding cytotoxicity values ($IC_{50}$) towards CCL228 cells only. In agreement relative cytotoxicity values, the active Mn(III) and Fe(III)-salen derivatives proportionally induced caspase-3/7 activation (FIG. 7 and Table 2). These results demonstrated that the level of caspase activation is correlated with the level of cytotoxicity (inversely correlated with the $IC_{50}$ values) which demonstrated that Mn(III)- and Fe(III) salen derivatives induced apoptosis via caspase 3/7 activation pathway.

As several of Mn(III)-salen complexes of the present invention showed tumor selective apoptosis in cultured cells, the inventors examined the efficacy of a Mn(III)-salen complex in down regulating tumor growth in a human cancer xenograft (implanted in mouse). All the animal experiments were carried out using the IACUC approved protocol.

Animal toxicity: The inventors analyzed the animal toxicity of 3,3'-dimethoxy Mn(III)-salen (compound 6), 3,3'-dihydroxy Mn(III)-salphen (compound 9) and 3,3'-dihydroxy Mn(III)-salnaphen (compound 16). The inventors intraperitoneally administered the Mn(III)-salen complexes (in PBS) at three different dozes (5, 10 and 20 mg/kg of mice, 6 weeks old normal C57B mice). The mice were treated twice a week for 4 weeks. After treatment, sign of toxicity were monitored (such as weight loss, mobility), animal behavior and health on a daily basis. The results demonstrated that these compounds did not have any significant animal toxicity at the doses treated (data not shown). All the mice survived without significant loss of body weight.

Xenograft experiment: To test the efficacy in controlling the tumor growth, the inventors administered compound compounds, 6, 9 and 16, intraperitoneally to six week old Athymic nude nu/nu mice carrying the colon cancer xenograft. In brief, $2\times10^6$ human colon cancer cells (CCL228 cell in 100 μl of PBS) were injected subcutaneously (near the right back limb). Animals were examined daily for signs of tumor growth and behavior. Once the tumor size reached ~25 $mm^2$ (2 to 3 weeks after injection of cells) the inventors administered compounds 6, 9, and 16 intraperitoneally (separately in PBS solution, twice a week, 10 mg/kg dose). Every study was performed in three parallel replicates. Control mouse were injected with equal volume of the diluent (PBS) alone. Prior to every new treatment with metallo-salens, bi-dimensional measurements were carried out using calipers and cross-sectional area (tumor size) and data were plotted in FIG. 8A.

Figure 8B:
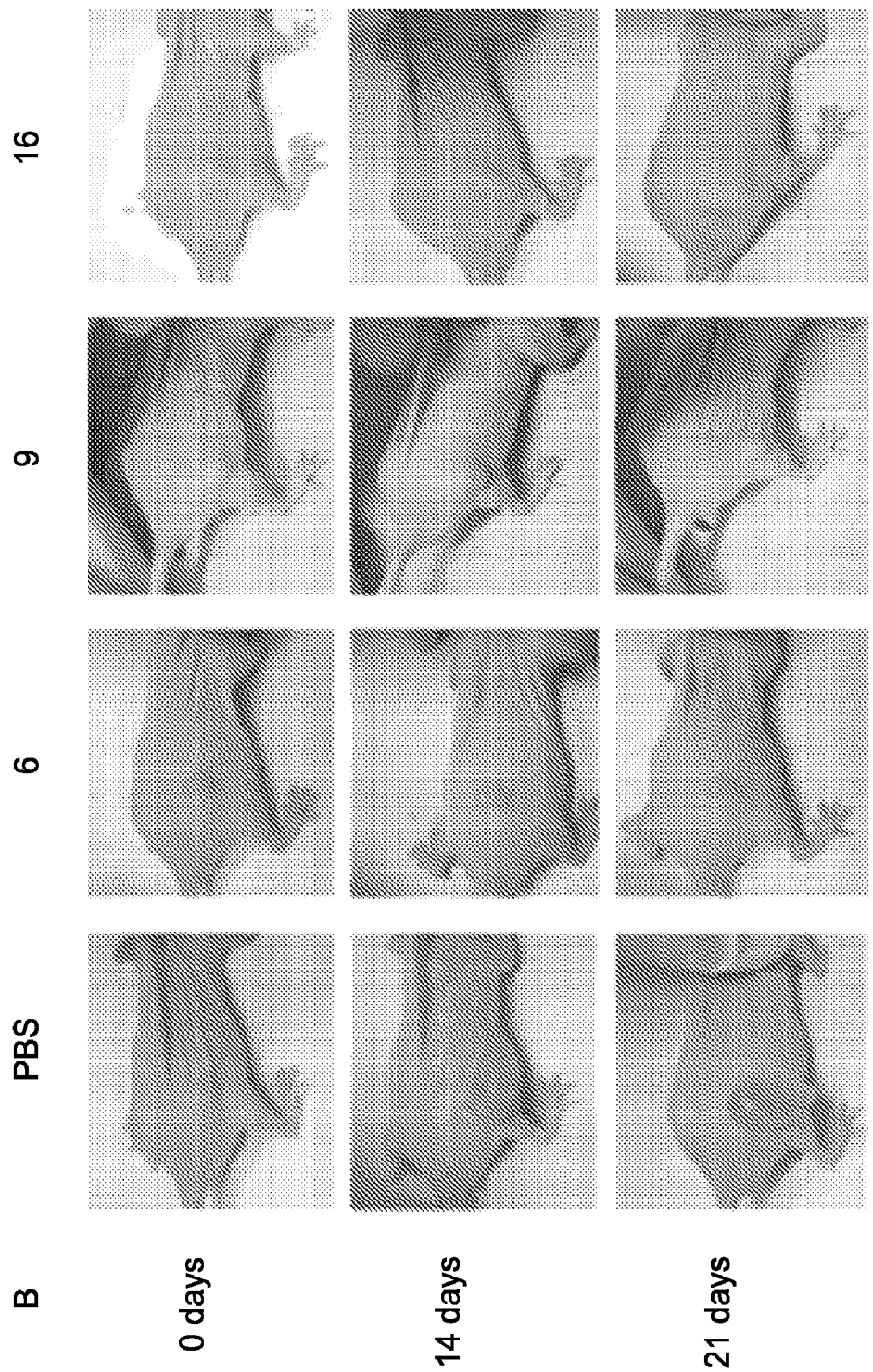

Application of the compounds 6 and 9 (3,3'-dimethoxy Mn(III)-salen and 3,3'-dihydroxy Mn(III)-salphen respectively) resulted in complete arrest of tumor growth while in the untreated control (PBS only) or the treatment with compounds 16, tumor size were grown exponentially (FIGS. 8A and 8B). These observations demonstrated that 3,3'-dimethoxy Mn(III)-salen (compound 6) and 3,3'-dihydroxy Mn(III)-salphen (compound 9) have potential antitumor activity in vivo. The results showing the suppression of tumor growth in colon cancer xenograft upon application of Mn(III)-salen complexes of the present invention demonstrate that they have strong potential for novel anticancer therapy, based on these results that apoptotically active Mn(III)-salen and Fe(III)-salen complexes of the present invention are potential novel anti-neoplastic agents.

Figure 9A:
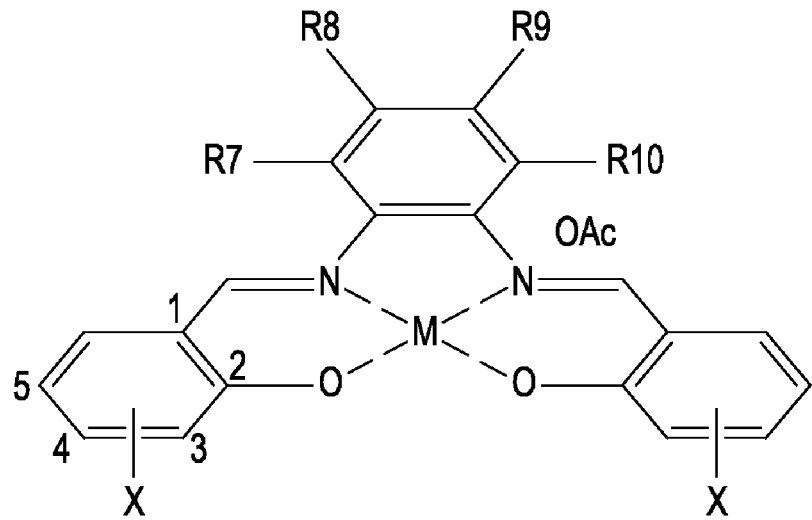
FIGS. 9A and 9B show some additional metallo-salen complexes with different attached substituents.
Figure 9B:
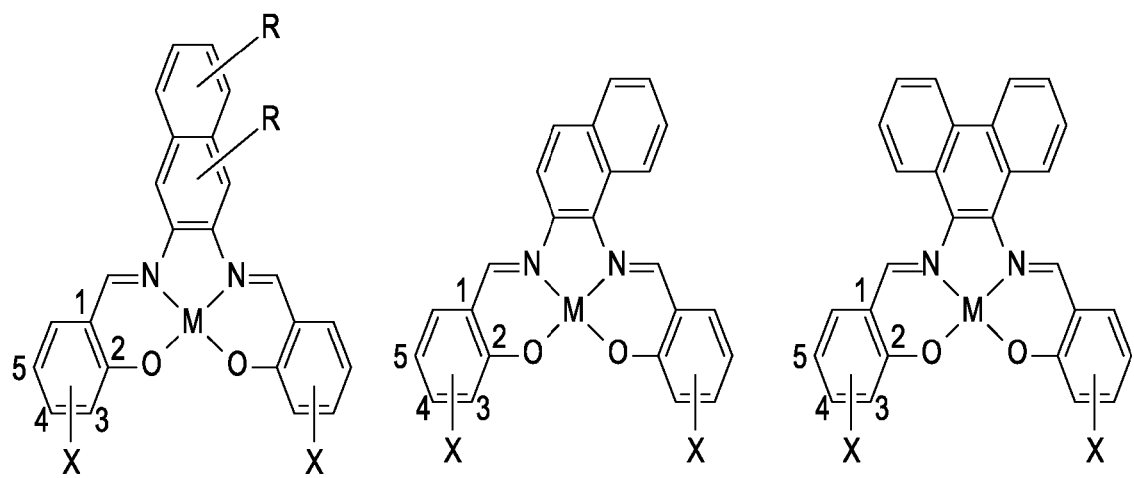

FIGS. 9A and 9B show the structure of some additional metallo-salen complexes with different substituent groups attached.

The present invention demonstrates that selective Mn(III)- and Fe(III)-salen derivatives induce apoptosis in breast and colon cancer cells with 2-5 fold preference over normal non malignant breast epithelial cells. The position and nature of the substituents, central metal ion and the structures of the metallo-salen play critical role in determining their apoptotic activities and can be applied to develop novel effective anti-tumor agents. More importantly, several Mn(III)-salen complexes of the present invention also suppressed the tumor growth in vivo (in colon cancer xenografts) indicating a strong potential for the Mn(III)- and Fe(III)-salen complexes of the present invention as anti-tumor agents.

It is contemplated that any embodiment discussed in this specification can be implemented with respect to any method, kit, reagent, or composition of the invention, and vice versa. Furthermore, compositions of the invention can be used to achieve methods of the invention.

It will be understood that particular embodiments described herein are shown by way of illustration and not as limitations of the invention. The principal features of this invention can be employed in various embodiments without departing from the scope of the invention. Those skilled in the art will recognize, or be able to ascertain using no more than routine experimentation, numerous equivalents to the specific procedures described herein. Such equivalents are considered to be within the scope of this invention and are covered by the claims.

All publications and patent applications mentioned in the specification are indicative of the level of skill of those skilled in the art to which this invention pertains. All publications and patent applications are herein incorporated by reference to the same extent as if each individual publication or patent application was specifically and individually indicated to be incorporated by reference.

The use of the word "a" or "an" when used in conjunction with the term "comprising" in the claims and/or the specification may mean "one," but it is also consistent with the meaning of "one or more," "at least one," and "one or more than one." The use of the term "or" in the claims is used to mean "and/or" unless explicitly indicated to refer to alternatives only or the alternatives are mutually exclusive, although the disclosure supports a definition that refers to only alternatives and "and/or." Throughout this application, the term "about" is used to indicate that a value includes the inherent variation of error for the device, the method being employed to determine the value, or the variation that exists among the study subjects.

As used in this specification and claim(s), the words "comprising" (and any form of comprising, such as "comprise" and "comprises"), "having" (and any form of having, such as "have" and "has"), "including" (and any form of including, such as "includes" and "include") or "containing" (and any form of containing, such as "contains" and "contain") are inclusive or open-ended and do not exclude additional, unrecited elements or method steps.

The term "or combinations thereof" as used herein refers to all permutations and combinations of the listed items preceding the term. For example, "A, B, C, or combinations thereof" is intended to include at least one of: A, B, C, AB, AC, BC, or ABC, and if order is important in a particular context, also BA, CA, CB, CBA, BCA, ACB, BAC, or CAB. Continuing with this example, expressly included are combinations that contain repeats of one or more item or term, such as BB, AAA, MB, BBC, AAABCCCC, CBBAAA, CABABB, and so forth. The skilled artisan will understand that typically there is no limit on the number of items or terms in any combination, unless otherwise apparent from the context.

All of the compositions and/or methods disclosed and claimed herein can be made and executed without undue experimentation in light of the present disclosure. While the compositions and methods of this invention have been described in terms of preferred embodiments, it will be apparent to those of skill in the art that variations may be applied to the compositions and/or methods and in the steps or in the sequence of steps of the method described herein without departing from the concept, spirit and scope of the invention. All such similar substitutes and modifications apparent to those skilled in the art are deemed to be within the spirit, scope and concept of the invention as defined by the appended claims.

REFERENCES

U.S. Pat. No. 7,122,537: Cyclic salen-metal compounds as scavengers for oxygen radicals and useful as antioxidants in the treatment and prevention of diseases.

United States Patent Application No. 20070142462: Method of treating cancer.

United States Patent Application No. 20070275944: Antioxidants and methods of their use.

(1) Basu, A.; Miura, A. Int J Mol Med 2002, 10, 541-5.
(2) Barnes, K. R.; Lippard, S. J. Met Ions Biol Syst 2004, 42, 143-77.
(3) Zhang, C. X.; Lippard, S. J. Current Opinion in Chemical Biology 2003, 7, 481-89.
(4) Brambilla, C.; Ferrari, L.; Passoni, P.; Bonadonna, G. Cancer Treat Rev 1993, 19 Suppl C, 3-9.
(5) Robson, H.; Meyer, S.; Shalet, S. M.; Anderson, E.; Roberts, S.; Eden, O. B. Med Pediatr Oncol 2002, 39, 573-80.
(6) Zhang, L.; Zhang, Y.; Huang, P. Y.; Xu, F.; Peng, P. J.; Guan, Z. Z. Cancer Chemother Pharmacol 2008, 61, 33-8.
(7) Boerner, L. J. K.; Zaleski, J. M. Current Opinion in Chemical Biology 2005, 9, 135-44.
(8) Ansari, K. I.; Mishra, B. P.; Mandal, S. S. Biochim Biophys Acta 2008, 1779, 66-73.
(9) Baruah, H.; Barry, C. G.; Bierbach, U. Current Topics in Medicinal Chemistry 2004, 4, 1537-49.
(10) Chow, C. S.; Barton, J. K. Methods in Enzymology 1992, 212, 219-42.
(11) Denison, C.; Kodadek, T. Chem Biol 1998, 5, R129-45.
(12) Dickinson, L. A.; Burnett, R.; Melander, C.; Edelson, B. S.; Arora, P. S.; Dervan, P. B.; Gottesfeld, J. M. Chem Biol 2004, 11, 1583-94.
(13) Fechter, E. J.; Olenyuk, B.; Dervan, P. B. Angew Chem Int Ed Engl 2004, 43, 3591-4.
(14) Guo, Z.; Zhou, D.; Schultz, P. G. Science 2000, 288, 2042-5.
(15) Hartinger, C. G.; Schluga, P.; Galanski, M.; Baumgartner, C.; Timerbaev, A. R.; Keppler, B. K. Electrophoresis 2003, 24, 2038-44.
(16) Kwon, Y.; Arndt, H. D.; Mao, Q.; Choi, Y.; Kawazoe, Y.; Dervan, P. B.; Uesugi, M. J Am Chem Soc 2004, 126, 15940-1.
(17) Majmudar, C. Y.; Mapp, A. K. Curr Opin Chem Biol 2005, 9, 467-74.
(18) Mapp, A. K.; Ansari, A. Z.; Ptashne, M.; Dervan, P. B. Proc Natl Acad Sci USA 2000, 97, 3930-5.
(19) Murphy, C. J.; Barton, J. K. Methods Enzymol 1993, 226, 576-94.
(20) Ott, I.; Gust, R. Arch Pharm (Weinheim) 2007, 340, 117-26.
(21) Perrin, D. M.; Mazumder, A.; Sigman, D. S. Progress in Nucleic Acid Research and Molecular Biology, Vol 52 1996, 52, 123-51.
(22) Zheng, P.; Tang, N.; Burrows, C. J.; Rokita, S. E. Faseb Journal 1994, 8, A1265-a1265.
(23) Zorbas, H.; Keppler, B. K. Chembiochem 2005, 6, 1157-66.
(24) Jacobsen, E. N.; Zhang, W.; Guler, M. L. Journal of the American Chemical Society 1991, 113, 6703-04.
(25) Bhattacharya, S.; Mandal, S. S. Chemical Communications 1996, 1515-16.
(26) Burrows, C. J.; Hickerson, R. P.; Muller, J. G.; Felden, B.; Rokita, S. E. Biophysical Journal 1999, 76, A5-a5.
(27) Czlapinski, J. L.; Sheppard, T. L. Journal of the American Chemical Society 2001, 123, 8618-19.
(28) Muller, J. G.; Paikoff, S. J.; Rokita, S. E.; Burrows, C. J. J Inorg Biochem 1994, 54, 199-206.
(29) Routier, S.; Bernier, J. L.; Waring, M. J.; Colson, P.; Houssier, C.; Bailly, C. Journal of Organic Chemistry 1996, 61, 2326-31.
(30) Gravert, D. J.; Griffin, J. H. Journal of Organic Chemistry 1993, 58, 820-22.
(31) Shrivastava, H. Y.; Devaraj, S. N.; Nair, B. U. Journal of Inorganic Biochemistry 2004, 98, 387-92.
(32) Rokita, S. E.; Burrows, C. J. 2003, 1, 126-45.
(33) Routier, S.; Vezin, H.; Lamour, E.; Bernier, J. L.; Catteau, J. P.; Bailly, C. Nucleic Acids Research 1999, 27, 4160-66.
(34) Doctrow, S. R.; Huffman, K.; Marcus, C. B.; Tocco, G.; Malfroy, E.; Adinolfi, C. A.; Kruk, H.; Baker, K.; Lazarowych, N.; Mascarenhas, J.; Malfroy, B. J Med Chem 2002, 45, 4549-58.
(35) Rong, Y.; Doctrow, S. R.; Tocco, G.; Baudry, M. Proc Natl Acad Sci USA 1999, 96, 9897-902.
(36) Woldemariam, G. A.; Mandal, S. S. J Inorg Biochem 2008, 102, 740-7.

(37) Gerloch, M., Lewis, J., Mabbs F. E., Richards, A. Journal of the Chemical Society [section] A: Inorganic, Physical and Theoretical 1968, 1, 112-16.

(38) Gravert, D. J.; Griffin, J. H. Metal Ions in Biological Systems, Vol 33 1996, 33, 515-36.

(39) Pavri, R.; Zhu, B.; Li, G.; Trojer, P.; Mandal, S.; Shilatifard, A.; Reinberg, D. Cell 2006, 125, 703-17.

(40). Zhu, B.; Mandal, S. S.; Pham, A. D.; Zheng, Y.; Erdjument-Bromage, H.; Batra, S. K.; Tempst, P.; Reinberg, D. Genes Dev 2005, 19, 1668-73.

(41) Mandal, G. W. a. S. S. J. Inorg. Biochem 2007, In Press.

(42) Awasthi, S.; Singhal, S. S.; He, N.; Chaubey, M.; Zimniak, P.; Srivastava, S. K.; Singh, S. V.; Awasthi, Y. C. Int J Cancer 1996, 68, 333-9.

(43) Nguyen S. M., L., C J., and Levin, L A. Journal of Neuroscience 2007, 161, 281-84.

(44) Park, M. S.; De Leon, M.; Devarajan, P. Journal of the American Society of Nephrology 2002, 13, 858-65.

(45) Ansari, A. Z.; Mapp, A. K. Current Opinion in Chemical Biology 2002, 6, 765-72.

(46) Balamurugan, K.; Rajaram, R.; Ramasami, T.; Narayanan, S. Free Radical Biology and Medicine 2002, 33, 1622-40.

(47) Barton, J. K. Science 1986, 233, 727-34.

(48) Borchardt, A.; Liberles, S. D.; Biggar, S. R.; Crabtree, G. R.; Schreiber, S. L. Chem Biol 1997, 4, 961-8.

(49) Copeland, K. D.; Lueras, A. M.; Stemp, E. D.; Barton, J. K. Biochemistry 2002, 41, 12785-97.

(50) Danford, A. J.; Wang, D.; Wang, Q.; Tullius, T. D.; Lippard, S. J. Proc Natl Acad Sci USA 2005, 102, 12311-6.

(51) Dias, N.; Jacquemard, U.; Baldeyrou, B.; Tardy, C.; Lansiaux, A.; Colson, P.; Tanious, F.; Wilson, W. D.; Routier, S.; Merour, J.Y.; Bailly, C. Biochemistry 2004, 43, 15169-78.

(52) Gottesfeld, J. M.; Neely, L.; Trauger, J. W.; Baird, E. E.; Dervan, P. B. Nature 1997, 387, 202-5.

(53) Liu, B.; Alluri, P. G.; Yu, P.; Kodadek, T. J Am Chem Soc 2005, 127, 8254-5.

(54) Mapp, A. K. Org Biomol Chem 2003, 1, 2217-20.

(55) Minter, A. R.; Brennan, B. B.; Mapp, A. K. J Am Chem Soc 2004, 126, 10504-5.

(56) Mote, J., Jr.; Ghanouni, P.; Reines, D. J Mol Biol 1994, 236, 725-37.

(57) Pyle, A. M.; Barton, J. K. Progress in Inorganic Chemistry 1990, 38, 413-475.

(58) Schreiber, S. Curr Biol 2004, 14, R292-3.

(59) Meares, C. F.; Datwyler, S. A.; Schmidt, B. D.; Owens, J.; Ishihama, A. Methods Enzymol 2003, 371, 82-106.

(60) Ozoline, O. N.; Fujita, N.; Ishihama, A. J Biol Chem 2000, 275, 1119-27.

(61) Kurahashi, T.; Kobayashi, Y.; Nagatomo, S.; Tosha, T.; Kitagawa, T.; Fujii, H. Inorg Chem 2005, 44, 8156-66.

What is claimed is:

1. A pharmaceutical composition comprising

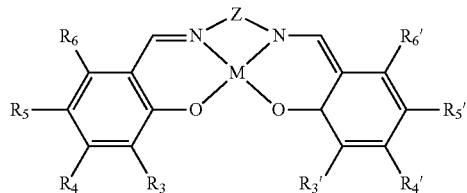

wherein Z is selected from a group comprising —(CH$_2$)$_2$, —(CH$_2$)$_3$, —(CH$_2$)$_4$, phenyl, naphthyl and benzoic acid, M is a metal selected from a group comprising Mn, Mn(II), Mn(III), Fe, Fe(II), Fe(III), Cu, Ni, Hg, Pt, Sc, Ti, V, Cr, Co, Zn, Y, Zr, Nb, Mo, Tc, Ru, Rh, Pd, Ag, Cd, Lu, Hf, Ta, W, Re, Os, Ir, Pt, and Au, $R_3$ and $R_3'$ are hydroxyl groups, $R_4$, $R_4'$, $R_5$, $R_5'$, $R_6$ and $R_6'$ are hydrogens, and wherein the composition is effective to treat a cancer, selected from a lymphoma, a blastoma, a tumor, a melanoma, ovarian cancer, breast cancer, non-small cell lung cancer, small cell lung cancer, renal cancer, colorectal cancer, pancreatic cancer, gastric cancer, bladder cancer, uterine cancer, lymphoma, and prostate cancer.

2. A pharmaceutical composition comprising

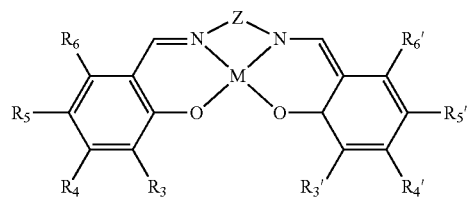

wherein Z is selected from a group comprising —(CH$_2$)$_2$, —(CH$_2$)$_3$, —(CH$_2$)$_4$, phenyl, naphthyl and benzoic acid, M is a metal selected from a group comprising Mn, Mn(II), Mn(III), Fe, Fe(II), Fe(III), Cu, Ni, Hg, Pt, Sc, Ti, V, Cr, Co, Zn, Y, Zr, Nb, Mo, Tc, Ru, Rh, Pd, Ag, Cd, Lu, Hf, Ta, W, Re, Os, Ir, Pt, and Au, $R_4$ and $R_4'$ are hydroxyl groups, $R_3$, $R_3'$, $R_5$, $R_5'$, $R_6$ and $R_6'$ are hydrogens, and wherein the composition is effective to treat a cancer, selected from a lymphoma, a blastoma, a tumor, a melanoma, ovarian cancer, breast cancer, non-small cell lung cancer, small cell lung cancer, renal cancer, colorectal cancer, pancreatic cancer, gastric cancer, bladder cancer, uterine cancer, lymphoma, and prostate cancer.

3. A pharmaceutical composition comprising

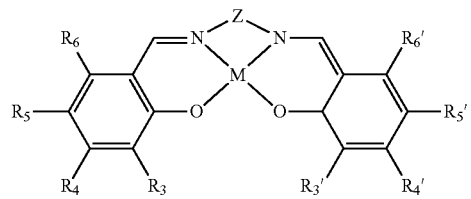

wherein Z is selected from a group comprising —(CH$_2$)$_2$, —(CH$_2$)$_3$, —(CH$_2$)$_4$, phenyl, naphthyl and benzoic acid, M is a metal selected from a group comprising Mn, Mn(II), Mn(III), Fe, Fe(II), Fe(III), Cu, Ni, Hg, Pt, Sc, Ti, V, Cr, Co, Zn, Y, Zr, Nb, Mo, Tc, Ru, Rh, Pd, Ag, Cd, Lu, Hf, Ta, W, Re, Os, Ir, Pt, and Au, $R_5$ and $R_5'$ are hydroxyl groups, $R_3$, $R_3'$, $R_4$, $R_4'$, $R_6$ and $R_6'$ are hydrogens, and wherein the composition is effective to treat a cancer, selected from a lymphoma, a blastoma, a tumor, a melanoma, ovarian cancer, breast cancer, non-small cell lung cancer, small cell lung cancer, renal cancer, colorectal cancer, pancreatic cancer, gastric cancer, bladder cancer, uterine cancer, lymphoma, and prostate cancer.

4. A method of synthesizing a metallo-salen compound and its derivatives comprising the steps of:

mixing an aldehyde selected from a group comprising salicylaldehyde, 2,3-dihydroxybenzaldehyde, 2,4-dihydroxybenzaldehyde, 2,5-dihydroxybenzaldehyde, 2-hydroxy-3-methoxybenzaldehyde, 2-hydroxy-4-methoxybenzaldehyde, and 2-hydroxy-5-methoxybenzaldehyde and a diamine or a diamino derivative selected from a group comprising ethylenediamine, o-phenylenediamine, phenylenediamine, 2,3-diaminonaphthalene, 1,3-diaminobutane, 1,4-diaminobutane, and 3,4-diaminobenzoic acid dissolved in an organic solvent to form a precipitate;

filtering the precipitate;

washing the precipitate with the organic solvent;

dissolving the precipitate in the organic solvent and mixing with an anhydrous metal dissolved in the organic solvent to form a liquid reaction mixture;

heating the liquid reaction mixture with stirring to form the metallo-salen compound (I); wherein Z is selected from a group comprising —(CH$_2$)$_2$, phenyl, naphthyl, —(CH$_2$)$_3$, —(CH$_2$)$_4$, and benzoic acid; M is a metal selected from a group comprising Fe, Mn, Cu, Ni, Hg, Pt, Sc, Ti, V, Cr, Co, Zn, Y, Zr, Nb, Mo, Tc, Ru, Rh, Pd, Ag, Cd, Lu, Hf, Ta, W, Re, Os, Ir, Pt, and Au; R$_3$ and R$_3$' are independently selected from a hydrogen, a hydroxyl group and a methoxy group; R$_4$ and R$_4$' are independently selected from a hydrogen, a hydroxyl group and a methoxy group; R$_5$ and R$_5$' are independently selected from a hydrogen, a hydroxyl group and a methoxy group; and R$_6$ and R$_6$' are hydrogens;

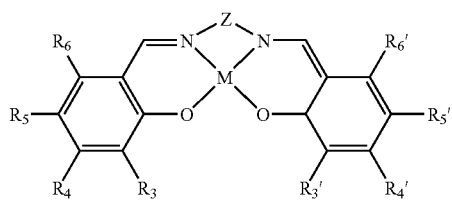
(I)

precipitating the synthesized metallo-salen compound (I) by cooling the liquid reaction mixture or by adding diethyl ether;

isolating the precipitated metallo-salen compound (I) by filtration or other physical separation methods; and recrystallizing the isolated metallo-salen compound (I) by dissolving in the organic solvent.

5. The method of claim 4, wherein the organic solvent comprises methanol, ethanol, acetone, iso-propyl alcohol, acetonitrile, benzene, ethyl acetate or any combinations thereof.

6. The method of claim 4, wherein the anhydrous metal is in the form of a salt, wherein the salt comprises an anion selected from a group comprising a chloride, an acetate, a halide, a carbonate, a nitrite, a nitrate, a perchlorate, a sulfate, a sulfide, and a hydroxide.

7. A method for treating a cancer in an subject comprising the steps of:

identifying a subject in need for treatment against the cancer; and providing a therapeutically effective amount of a composition sufficient to treat the cancer comprising:

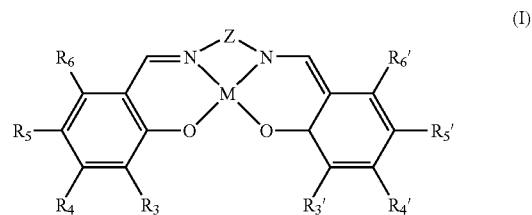
(I)

wherein Z is selected from a group comprising —(CH$_2$)$_2$, phenyl, naphthyl, —(CH$_2$)$_3$, —(CH$_2$)$_4$, and benzoic acid; M is a metal selected from a group comprising Fe, Mn, Cu, Ni, Hg, Pt, Sc, Ti, V, Cr, Co, Zn, Y, Zr, Nb, Mo, Tc, Ru, Rh, Pd, Ag, Cd, Lu, Hf, Ta, W, Re, Os, Ir, Pt, and Au; R$_3$ and R$_3$' are independently selected from a hydrogen, a hydroxyl group and a methoxy group; R$_4$ and R$_4$' are independently selected from a hydrogen, a hydroxyl group and a methoxy group; R$_5$ and R$_5$' are independently selected from a hydrogen, a hydroxyl group and a methoxy group; and R$_6$ and R$_6$' are hydrogens.

8. The method of claim 7, wherein the cancer comprises a melanoma, ovarian cancer, breast cancer, non-small cell lung cancer, small cell lung cancer, renal cancer, colorectal cancer, pancreatic cancer, gastric cancer, bladder cancer, uterine cancer, lymphoma, and prostate cancer.

* * * * *